US011801493B2

(12) United States Patent
Matusz et al.

(10) Patent No.: US 11,801,493 B2
(45) Date of Patent: Oct. 31, 2023

(54) METHODS FOR CONDITIONING AN ETHYLENE EPOXIDATION CATALYST AND ASSOCIATED METHODS FOR THE PRODUCTION OF ETHYLENE OXIDE

(71) Applicant: SHELL OIL COMPANY, Houston, TX (US)

(72) Inventors: Marek Matusz, Houston, TX (US); Robert Lewis Paddock, Houston, TX (US); Randall Clayton Yeates, Sugar Land, TX (US); John Robert Lockemeyer, Sugar Land, TX (US)

(73) Assignee: SHELL USA, INC., Houston, TX (US)

( * ) Notice: Subject to any disclaimer, the term of this patent is extended or adjusted under 35 U.S.C. 154(b) by 821 days.

(21) Appl. No.: 16/465,445

(22) PCT Filed: Nov. 29, 2017

(86) PCT No.: PCT/US2017/063651
§ 371 (c)(1),
(2) Date: May 30, 2019

(87) PCT Pub. No.: WO2018/102377
PCT Pub. Date: Jun. 7, 2018

(65) Prior Publication Data
US 2020/0001277 A1 Jan. 2, 2020

Related U.S. Application Data

(60) Provisional application No. 62/429,111, filed on Dec. 2, 2016.

(51) Int. Cl.
*C07D 301/10* (2006.01)
*B01J 23/68* (2006.01)
(Continued)

(52) U.S. Cl.
CPC ............. *B01J 23/688* (2013.01); *B01J 37/08* (2013.01); *B01J 37/14* (2013.01); *C07D 301/10* (2013.01); *C07D 303/04* (2013.01)

(58) Field of Classification Search
None
See application file for complete search history.

(56) References Cited

U.S. PATENT DOCUMENTS 1,002,575 A 9/1911 Fried
2,219,575 A 10/1940 McNamee et al.
(Continued)

FOREIGN PATENT DOCUMENTS

EP 0003642 A2 8/1979
EP 0026605 A2 4/1981
(Continued)

OTHER PUBLICATIONS

International Search Report and Written Opinion received for PCT Patent Application No. PCT/US2017/063651, dated Feb. 7, 2018, 10 pages.
(Continued)

*Primary Examiner* — Coris Fung
*Assistant Examiner* — Keling Zhang
(74) *Attorney, Agent, or Firm* — SHELL USA, INC.

(57) ABSTRACT

Methods for conditioning an ethylene epoxidation catalyst are provided. The conditioning methods comprise contacting an ethylene epoxidation catalyst comprising a carrier, having silver and a rhenium promoter deposited thereon, with a conditioning feed gas comprising oxygen for a period of time of at least 2 hours at a temperature that is above 180° C. and at most 250° C., wherein the contacting of the ethylene epoxidation catalyst with the conditioning feed gas
(Continued)

occurs in an epoxidation reactor and in the absence of ethylene. Associated methods for the epoxidation of ethylene are also provided.

6 Claims, 3 Drawing Sheets

(51) Int. Cl.
*B01J 37/08* (2006.01)
*B01J 37/14* (2006.01)
*C07D 303/04* (2006.01)

(56) References Cited

U.S. PATENT DOCUMENTS

| | | | |
|---|---|---|---|
| 2,279,469 A | 4/1942 | Law et al. |
| 2,773,844 A | 12/1956 | Carlson et al. |
| 3,702,259 A | 11/1972 | Nielsen |
| 3,950,507 A | 4/1976 | Kuklina et al. |
| 3,962,136 A | 6/1976 | Nielsen et al. |
| 3,962,286 A | 6/1976 | Antonelli et al. |
| 4,007,135 A | 2/1977 | Hayden et al. |
| 4,097,414 A | 6/1978 | Cavitt |
| 4,102,820 A | 7/1978 | Cavitt |
| 4,206,128 A | 6/1980 | Cavitt |
| 4,224,194 A | 9/1980 | Cavitt |
| 4,242,235 A | 12/1980 | Cognion et al. |
| 4,321,206 A | 3/1982 | Cavitt |
| 4,379,134 A | 4/1983 | Weber et al. |
| 4,389,338 A | 6/1983 | Mitsuhata et al. |
| 4,400,559 A | 8/1983 | Bhise |
| 4,410,453 A | 10/1983 | Kiovsky et al. |
| 4,428,863 A | 1/1984 | Fry |
| 4,430,312 A | 2/1984 | Eickmeyer |
| 4,465,754 A | 8/1984 | Kuin et al. |
| 4,471,071 A | 9/1984 | Rebsdat et al. |
| 4,508,927 A | 4/1985 | Bhise et al. |
| 4,555,501 A | 11/1985 | Armstrong |
| 4,645,754 A | 2/1987 | Tamura et al. |
| 4,729,826 A | 3/1988 | Lindsay et al. |
| 4,761,394 A | 8/1988 | Lauritzen |
| 4,766,105 A | 8/1988 | Lauritzen |
| 4,808,738 A | 2/1989 | Lauritzen |
| 4,820,675 A | 4/1989 | Lauritzen |
| 4,822,900 A | 4/1989 | Hayden |
| 4,831,162 A | 5/1989 | Nakajima et al. |
| 4,845,296 A | 7/1989 | Ahmed et al. |
| 4,874,879 A | 10/1989 | Lauritzen et al. |
| 4,908,343 A | 3/1990 | Bhasin |
| 4,916,243 A | 4/1990 | Bhasin et al. |
| 4,921,681 A | 5/1990 | Ozero et al. |
| 4,939,114 A | 7/1990 | Nojiri et al. |
| 4,994,588 A | 2/1991 | Kapicak et al. |
| 5,051,395 A | 9/1991 | Mitchell et al. |
| 5,057,481 A | 10/1991 | Bhasin |
| 5,063,195 A | 11/1991 | Jin et al. |
| 5,081,096 A | 1/1992 | Monnier et al. |
| 5,100,859 A | 3/1992 | Gerdes et al. |
| 5,102,848 A | 4/1992 | Soo et al. |
| 5,112,795 A | 5/1992 | Minahan et al. |
| 5,145,658 A | 9/1992 | Chao |
| 5,155,242 A | 10/1992 | Shankar et al. |
| 5,364,826 A | 11/1994 | Kemp |
| 5,374,738 A | 12/1994 | Boen et al. |
| 5,380,697 A | 1/1995 | Matusz et al. |
| 5,395,812 A | 3/1995 | Nagase et al. |
| 5,407,888 A | 4/1995 | Herzog et al. |
| 5,418,202 A | 5/1995 | Evans et al. |
| 5,428,202 A | 6/1995 | Rossi |
| 5,444,034 A | 8/1995 | Rizkalla et al. |
| 5,447,897 A | 9/1995 | Kemp |
| 5,486,628 A | 1/1996 | Kemp |
| 5,504,053 A | 4/1996 | Chou et al. |
| 5,646,087 A | 7/1997 | Rizkalla et al. |
| 5,736,483 A | 4/1998 | Rizkalla et al. |
| 5,739,075 A | 4/1998 | Matusz |
| 5,770,746 A | 6/1998 | Cooker et al. |
| 5,780,656 A | 7/1998 | Rizkalla et al. |
| 5,801,259 A | 9/1998 | Kowaleski |
| 5,840,932 A | 11/1998 | Evans et al. |
| 5,854,167 A | 12/1998 | Rizkalla et al. |
| 5,856,534 A | 1/1999 | Cooker et al. |
| 5,905,161 A | 5/1999 | Boeck et al. |
| 6,040,467 A | 3/2000 | Papavassiliou et al. |
| 6,080,897 A | 6/2000 | Kawabe |
| 6,368,998 B1 | 4/2002 | Lockemeyer |
| 6,372,925 B1 | 4/2002 | Evans et al. |
| 6,452,027 B1 | 9/2002 | Billig et al. |
| 6,498,122 B2 | 12/2002 | Nakashiro |
| 6,511,938 B1 | 1/2003 | Liu et al. |
| 6,533,843 B2 | 3/2003 | Billig et al. |
| 6,579,825 B2 | 6/2003 | Lockemeyer |
| 6,600,056 B1 | 7/2003 | Mikawa et al. |
| 6,656,874 B2 | 12/2003 | Lockemeyer |
| 6,750,173 B2 | 6/2004 | Rizkalla et al. |
| 6,762,311 B2 | 7/2004 | Rizkalla et al. |
| 6,908,879 B1 | 6/2005 | Shima et al. |
| 7,102,022 B2 | 9/2006 | Evans et al. |
| 7,193,094 B2 | 3/2007 | Chipman et al. |
| 7,485,597 B2 | 2/2009 | Lockemeyer et al. |
| 7,553,980 B2 | 6/2009 | Rizkalla et al. |
| 8,530,682 B2 | 9/2013 | Sachs et al. |
| 8,871,677 B2 | 10/2014 | Richard et al. |
| 8,932,979 B2 | 1/2015 | Matusz et al. |
| 2003/0162984 A1 | 8/2003 | Lockemeyer et al. |
| 2003/0191019 A1 | 10/2003 | Rizkalla et al. |
| 2004/0198993 A1 | 10/2004 | Matusz et al. |
| 2007/0185339 A1 | 8/2007 | Lu |
| 2007/0225511 A1 | 9/2007 | Bortinger et al. |
| 2008/0306291 A1 | 12/2008 | Billig et al. |
| 2009/0069583 A1 | 3/2009 | Rizkalla et al. |
| 2009/0234144 A1 | 9/2009 | Bos et al. |
| 2010/0016617 A1 | 1/2010 | Pak et al. |

FOREIGN PATENT DOCUMENTS

| | | |
|---|---|---|
| EP | 0038446 A2 | 10/1981 |
| EP | 0211521 A1 | 2/1987 |
| EP | 0226234 A1 | 6/1987 |
| EP | 0266015 A1 | 5/1988 |
| EP | 0326392 A1 | 8/1989 |
| EP | 0327356 A1 | 8/1989 |
| EP | 0352850 A1 | 1/1990 |
| EP | 0425020 A1 | 5/1991 |
| EP | 0448157 A1 | 9/1991 |
| EP | 0496470 A1 | 7/1992 |
| EP | 0567273 A1 | 10/1993 |
| EP | 0716884 A2 | 6/1996 |
| EP | 0764464 A2 | 3/1997 |
| EP | 0806984 A1 | 11/1997 |
| EP | 0808215 A1 | 11/1997 |
| EP | 0933130 A2 | 8/1999 |
| EP | 1002575 A2 | 5/2000 |
| EP | 1618100 B1 | 1/2006 |
| GB | 1170663 A | 11/1969 |
| GB | 1191983 A | 5/1970 |
| GB | 1489335 A | 10/1977 |
| JP | H04346835 A | 12/1992 |
| NO | 0017946 A2 | 3/2000 |
| SU | 1255200 A1 | 9/1986 |
| WO | 9505896 A1 | 3/1995 |
| WO | 9604989 A1 | 2/1996 |
| WO | 9740933 A1 | 11/1997 |
| WO | 9746317 A1 | 12/1997 |
| WO | 9845280 A1 | 10/1998 |
| WO | 9952883 A1 | 10/1999 |
| WO | 0015332 A1 | 3/2000 |
| WO | 2004002917 A1 | 1/2004 |
| WO | 2004002971 A1 | 1/2004 |
| WO | 2004078736 A1 | 9/2004 |
| WO | 2004078737 A1 | 9/2004 |
| WO | 2004092148 A2 | 10/2004 |
| WO | 2004101141 A1 | 11/2004 |

(56) References Cited

FOREIGN PATENT DOCUMENTS

| WO | 2005097318 A1 | 10/2005 | |
| WO | 2006020718 A2 | 2/2006 | |
| WO | WO-2012141942 A1 * | 10/2012 | ............. B01J 23/50 |

OTHER PUBLICATIONS

International Search Report for PCT Patent Application No. PCT/US03/19827, dated Jun. 11, 2004, 4 pages.
Written Opinion received for PCT Patent Application No. PCT/US03/19827, dated Jul. 16, 2004, 5 pages.
International Search Report received for PCT Patent Application No. PCT/US03/20095, dated Feb. 20, 2004, 3 pages.
Written Opinion received for PCT Patent Application No. PCT/US03/20095, dated Mar. 16, 2004, 7 pages.
International Search Report for and Written Opinion PCT Patent Application No. PCT/US2004/010457, dated Jan. 18, 2005, 16 pages.
Kirk-Othmer, Encyclopedia of Chemical Technology, 3rd Edition, vol. 9, 1980, pp. 445-447.
Perry et al., Perry's Chemical Engineers Handbook, 6th edition, 1984, pp. 20-14 to 20-51.
Jerry, "Reactions, Mechanisms and Structure", Advanced Organic Chemistry, 3rd Edition, 1985, p. 332.
Kirk-Othmer, Encyclopedia of Chemical Technology, 4th Edition, vol. 9, 1994, pp. 915-959.
Mansfield, Statistics for Business and Economics, Methods and Applications, second Edition, p. 34.
Brunauer et al., "Adsorption of Gases in Multimolecular Layers", Journal of American Chemical Society, vol. 60, Issue No. 2, Feb. 1938, pp. 309-319.
Beilstein institute for Organic Chemistry, American Chemical Society, vol. 56, 1934, pp. 1870-1872, XP002296657.
Schouten et al., Oxidation of Ethene in a Wall-cooled Packed Bed Reactor, Chemical Engineering Science, vol. 49, Issue No. 24A, 1994, pp. 4725-4747.
Kobe et al., Encyclopedia of Catalysis, vol. 3, Dec. 2002, p. 246.
International Search Report and Written Opinion received for PCT Patent Application No. PCT/US2009/042765, dated Nov. 18, 2009, 15 pages.
Rebsdat et al., "Ethylene Oxide", Ullmann's Encyclopedia of Industrial Chemistry, vol. A10, 2007, pp. 117-135.
Monnier et al., "Effects of Chlorine and Chlorine Dynamics During Silver-catalyzed Epoxidation of Butadiene", Journal of catalysis, vol. 226, 2004, pp. 321-333.
Zhou et al., "Optimization Fixed-bed Reactor for Ethylene Epoxidation", Chemical Engineering and Processing, vol. 44, 2005, pp. 1098-1107.
Jankowiak et al., "Ethylene Epoxidation Over Silver and Coppersilver Bimetallic Catalyst: Ii. CS and Cl Promotion", Journal of Catalysis, vol. 236, 2005, pp. 379-386.
Linic et al., "Construction of a Reaction Coordinate and a Microkinetic Model for Ethylene Epoxidation on Silver from DFT Calculations and Surface Science Experiments", Journal of Catalysis, vol. 214, 2003, pp. 200-212.
Berty, "Inhibitor Action of Chlorinated Hydrocarbons in Oxidation of Ethylene to Ethylene Oxide", Chemical Engineering Comm., vol. 82, 1989, pp. 229-232.

* cited by examiner

METHODS FOR CONDITIONING AN ETHYLENE EPOXIDATION CATALYST AND ASSOCIATED METHODS FOR THE PRODUCTION OF ETHYLENE OXIDE

CROSS-REFERENCE TO RELATED APPLICATIONS

The present application is a National Stage (§ 371) of International Application No. PCT/US2017/063651, filed Nov. 29, 2017, which claims priority from U.S. Provisional Application No. 62/429,111, filed Dec. 2, 2016, the disclosures of each of which are hereby incorporated by reference in their entirety.

BACKGROUND OF THE INVENTION

Ethylene oxide is a valuable raw material that is well-known for its use as a versatile chemical intermediate in the production of a wide variety of chemicals and products. For example, ethylene oxide is used to produce ethylene glycol, which is used in many diverse applications and may be found in a variety of products, including automotive engine antifreeze, hydraulic brake fluids, resins, fibers, solvents, paints, plastics, films, household and industrial cleaners, pharmaceutical preparations, and personal care items, such as cosmetics, shampoos, etc.

Ethylene oxide is formed by reacting ethylene with oxygen in the presence of a silver-based ethylene epoxidation catalyst. The selectivity of an ethylene epoxidation catalyst, also known as the "efficiency", refers to the ability of the epoxidation catalyst to convert ethylene to the desired reaction product, ethylene oxide, versus the competing by-products (e.g., $CO_2$ and $H_2O$), and is typically expressed as the percentage of the number of moles of ethylene oxide produced per number of moles of ethylene reacted.

Modern silver-based ethylene epoxidation catalysts are highly selective towards the production of ethylene oxide and can achieve selectivity values that exceed the theoretically maximal selectivity of 6/7 or 85.7 mole-%, which is based on the stoichiometry of the reaction equation:

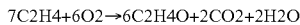

$$7C_2H_4 + 6O_2 \rightarrow 6C_2H_4O + 2CO_2 + 2H_2O$$

Cf. Kirk-Othmer's Encyclopedia of Chemical Technology, 4th ed., Vol. No. 9, 1994, p. 926. Such "high selectivity" catalysts, which typically comprise silver, a rhenium promoter, and optionally one or more additional promoters, such as alkali metals (e.g., cesium, lithium, etc.), alkaline earth metals (e.g., magnesium), transition metals (e.g., tungsten), and main group non-metals (e.g., sulfur), are disclosed, for example, in U.S. Pat. Nos. 4,761,394 and 4,766,105.

To a large extent, selectivity determines the economical attractiveness of an ethylene epoxidation process. For example, on a commercial scale, even slight, e.g., 1%, increases in selectivity of the epoxidation process can reduce the yearly operating costs of a large-scale ethylene oxide plant substantially. Accordingly, much research has been devoted to improving catalyst selectivity and to find process conditions which enable full exploitation of catalyst performance.

High selectivity catalysts can be conditioned prior to start-up of the epoxidation reaction in order to remove residual organic compounds or ammonia from the catalyst manufacturing or to improve catalyst performance (e.g. activity and/or selectivity). Conditioning processes may take place prior to the start of ethylene oxide production and generally involve contacting the catalyst with a non-reactive feed gas. The duration and conditions of the catalyst bed during the conditioning period, such as feed gas composition and temperature, can significantly influence the catalyst performance that is observed after stable operation is reached. Thus, a need has arisen for conditioning methods that provide improved catalyst performance.

SUMMARY OF THE INVENTION

A method for conditioning an ethylene epoxidation catalyst is provided. The conditioning method comprises contacting an ethylene epoxidation catalyst comprising a carrier, having silver and a rhenium promoter deposited thereon, with a conditioning feed gas comprising oxygen for a period of time of at least 2 hours at a temperature that is above 180° C. and at most 250° C., wherein the contacting of the ethylene epoxidation catalyst with the conditioning feed gas occurs in an epoxidation reactor and in the absence of ethylene.

A method for the epoxidation of ethylene is also provided which comprises contacting an ethylene epoxidation catalyst comprising a carrier, having silver and a rhenium promoter deposited thereon, with a conditioning feed gas comprising oxygen for a period of time of at least 2 hours at a temperature that is above 180° C. and at most 250° C., wherein the contacting of the ethylene epoxidation catalyst with the conditioning feed gas occurs in an epoxidation reactor and in the absence of ethylene; and subsequently contacting the ethylene epoxidation catalyst in the epoxidation reactor with an epoxidation feed gas comprising ethylene, oxygen and an organic chloride.

A method for improving the selectivity of an ethylene epoxidation catalyst in an ethylene epoxidation process is also provided which comprises contacting an ethylene epoxidation catalyst comprising a carrier, having silver and a rhenium promoter deposited thereon, with a conditioning feed gas comprising oxygen for a period of time of at least 2 hours at a temperature that is above 180° C. and at most 250° C., wherein the contacting of the ethylene epoxidation catalyst with the conditioning feed gas occurs in an epoxidation reactor and in the absence of ethylene; and subsequently contacting the ethylene epoxidation catalyst in the epoxidation reactor with an epoxidation feed gas comprising ethylene, oxygen and an organic chloride.

DRAWINGS

Some specific example embodiments of the disclosure may be understood by referring, in part, to the following description and the accompanying drawings.

Figure 1A:
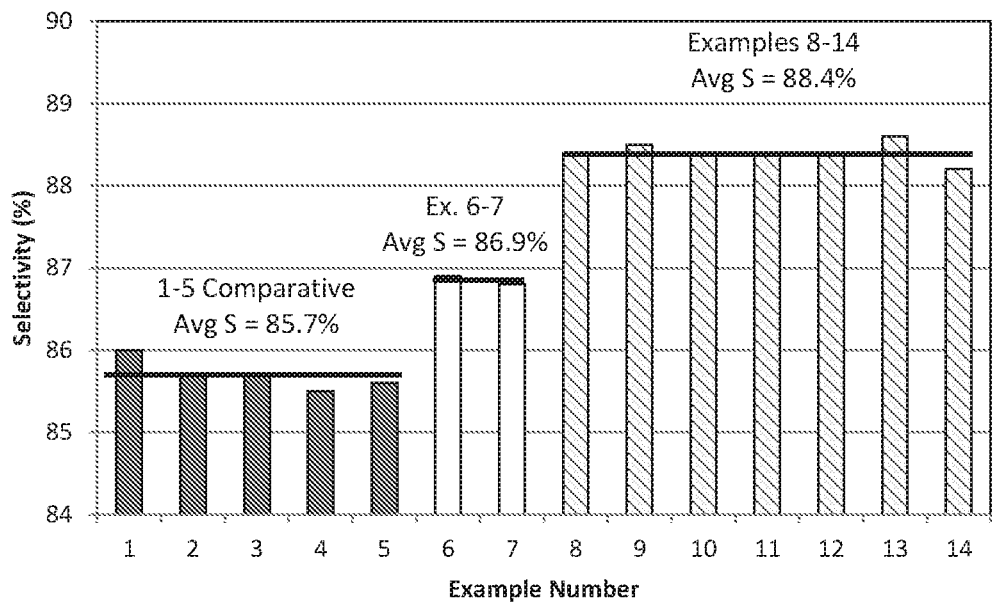
FIG. 1A is a bar chart of Experiments 1-14, showing an average selectivity of 85.7% for Comparative Examples 1-5, an average selectivity of 86.9% for Examples 6 and 7, and an average selectivity of 88.4% for Examples 8-14.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DETAILED DESCRIPTION OF THE INVENTION

The present disclosure provides methods for the conditioning of an ethylene epoxidation catalyst and associated methods for the epoxidation of ethylene. As explained in detail below, it has been found that by contacting an ethylene epoxidation catalyst comprising a carrier, having silver and a rhenium promoter deposited thereon, with a conditioning feed gas comprising oxygen for a period of time of at least 2 hours at a temperature that is above 180° C. and at most 250° C., wherein the contacting of the ethylene epoxidation catalyst with the conditioning feed gas occurs in the absence of ethylene, unexpected improvements in catalyst performance are obtained.

In particular, the conditioning methods of the present disclosure allow an ethylene epoxidation catalyst comprising a carrier, having silver and a rhenium promoter deposited thereon, to achieve a higher maximum catalyst selectivity than the same ethylene epoxidation catalyst would otherwise achieve using conventional catalyst conditioning methods or using no conditioning methods. Similarly, the conditioning methods of the present disclosure may also allow an ethylene epoxidation catalyst comprising a carrier, having silver and a rhenium promoter deposited thereon, to achieve an overall higher average catalyst selectivity and/or higher ethylene oxide production than the same ethylene epoxidation catalyst would otherwise achieve using conventional catalyst conditioning methods or using no conditioning methods.

In addition, an ethylene epoxidation catalyst conditioned in accordance with the conditioning methods of the present disclosure may also advantageously exhibit a lower oxygen conversion level at the point when a start-up feed gas comprising ethylene and oxygen is introduced than the same ethylene epoxidation catalyst would otherwise demonstrate. This is particularly beneficial as it allows for a process that is more stable, easily controllable and thereby safer. The lower oxygen conversion level can result in quicker breakthrough of the oxygen into the outlet of the reactor, which may allow a faster buildup of oxygen concentration in the reactor gas loop. This allows for the oxygen concentration in the start-up feed gas and/or the oxygen feed rate to be increased at a faster rate, which can significantly reduce the amount of time that is required before an oxygen concentration is achieved that is the same or substantially the same concentration as in the epoxidation feed gas utilized during normal ethylene oxide production. Furthermore, the methods disclosed herein may have other advantages, such as significantly reducing the duration of the start-up process and/or improving the overall profitability of the epoxidation process.

Although the conditioning and ethylene epoxidation methods described herein may be carried out in many ways, it is preferred that they be carried out as a gas phase process, i.e. a process in which a feed is contacted in the gas phase with an ethylene epoxidation catalyst which is present as a solid material, typically in a packed bed of a multi-tubular epoxidation reactor. Generally, the ethylene epoxidation process is carried out as a continuous process. The epoxidation reactor is typically equipped with heat exchange facilities to heat or cool the catalyst. The methods provided herein may be applied to fresh catalysts, as well as to aged catalysts that are being re-started following a prolonged and/or unexpected shut-down period.

In addition, the methods provided herein may also be applied to a precursor of an ethylene epoxidation catalyst (i.e., a carrier comprising silver in unreduced (cationic) form and further comprising the components necessary for obtaining, after reduction, an ethylene epoxidation catalyst comprising a carrier, having silver and a rhenium promoter deposited thereon). In this case, reduction may be effected by contacting the precursor with a conditioning feed gas comprising oxygen.

In general, an ethylene epoxidation catalyst comprising a carrier, having silver and a rhenium promoter deposited thereon, is heated up in an epoxidation reactor to a temperature that is above 180° C. and at most 250° C. using an external heat source, such as a coolant heater. For example, coolant may be heated using an external heat source (e.g. a coolant heater) and supplied to a coolant circuit of the epoxidation reactor. The heated coolant supplied to the coolant circuit of the reactor transfers heat to the ethylene epoxidation catalyst in the reactor, thereby raising the temperature to above 180° C. and at most 250° C.

It should be noted that the temperature values used herein refer to the gas phase temperature(s) in the catalyst bed as measured directly through the use of one or more thermocouples. As is known to those of ordinary skill in the art, as a means of monitoring the temperature in a multi-tubular epoxidation reactor, one or more axially positioned thermocouples may be placed in selected reactor tubes. Typically, an epoxidation reactor will contain a total of about 1,000 to about 12,000 reactor tubes, of which reactor tubes between 5 and 50, preferably between 5 and 30 will contain thermocouples. A thermocouple typically runs the entire length of the reactor tube and is usually centered within the tube by one or more positioning devices. Preferably, each thermocouple has 5-10 measurement points along its length (e.g. a multi-point thermocouple) to allow the operator to observe the temperature profile in the catalyst bed. It is within the ability of one skilled in the art to determine which specific reactor tubes within the reactor should contain a thermocouple and where they should be placed so as to permit meaningful and representative measurements. For the sake of accuracy, it is preferred that a plurality of equally spaced thermocouples are utilized, in which case the temperature of a catalyst bed having a relatively uniform loading density would be calculated by taking a numerical average of the plurality of gas temperature measurements, as is known to those of skill in the art.

Optionally, prior to contacting an ethylene epoxidation catalyst with a conditioning feed gas comprising oxygen for a period of time of at least 2 hours at a temperature that is above 180° C. and at most 250° C., the epoxidation catalyst may be contacted with a sweeping gas, which is typically an inert gas, such as nitrogen, argon, methane, etc. or combination thereof, at any suitable temperature. It may be particularly advantageous to contact the ethylene epoxidation catalyst with a sweeping gas at a temperature that is above 150° C. so as to convert a significant portion of organic nitrogen compounds that may have been used in the manufacture of the ethylene epoxidation catalyst to nitrogen-containing gases, which are swept up in the gas stream and removed from the catalyst. In addition, any moisture may be removed from the catalyst. The start-up of used ethylene epoxidation catalysts may or may not require the use of a sweeping gas, but it may frequently be used. Further details on these procedures may be found in U.S. Pat. No. 4,874,879, which is incorporated herein by reference.

In accordance with the methods of the present disclosure, after the epoxidation catalyst has reached a temperature that is above 180° C. and at most 250° C., it is contacted with a conditioning feed gas comprising oxygen for a period of time of at least 2 hours. As previously mentioned, the ethylene epoxidation catalyst is contacted with the conditioning feed gas in the absence of ethylene, thereby ensuring that the reaction between ethylene and oxygen does not take place during this period of time. It should be noted that the temperature at which the conditioning feed gas is first introduced to the ethylene epoxidation catalyst is not limited and thus, in some embodiments, the conditioning feed gas may be initially introduced at a temperature that is below 180° C., and optionally, may be introduced before, after or simultaneously with a sweeping gas (if used).

Typically, the ethylene epoxidation catalyst is contacted with the conditioning feed gas at a temperature that is above 180° C. and at most 250° C., or from at least 185° C. to at most 250° C., or from at least 190° C. to at most 250° C., or from at least 195° C. to at most 250° C., or from at least 200° C. to at most 250° C., or from above 180° C. to at most 245° C., or from at least 185° C. to at most 245° C., or from at least 190° C. to at most 245° C., or from at least 195° C. to at most 245° C., or from at least 200° C. to at most 245° C., or from above 180° C. to at most 240° C., or from at least 185° C. to at most 240° C., or from at least 190° C. to at most 240° C., or from at least 195° C. to at most 240° C., or from at least 200° C. to at most 240° C., or from at least 220° C. to at most 250° C., or from at least 220° C. to at most 245° C., or from at least 220° C. to at most 240° C., or from above 180° C. to at most 220° C., or from at least 185° C. to at most 220° C., or from at least 190° C. to at most 220° C., or from at least 195° C. to at most 220° C., or from at least 200° C. to at most 220° C.

Further, the ethylene epoxidation catalyst is contacted with the conditioning feed gas at one or more temperatures in the above temperature range for a period of time of at least 2 hours, typically from 2 to 200 hours, or from 2 to 100 hours, or from 2 to 72 hours, or from 2 to 48 hours, or from 2 to 36 hours, or from 2 to 24 hours, or from 6 to 200 hours, or from 6 to 72 hours, or from 6 to 48 hours, or from 6 to 36 hours, or from 6 to 24 hours, or from 12 to 72 hours, or from 12 to 48 hours, or from 12 to 36 hours, or from 12 to 24 hours, or from 24 to 48 hours. Although the ethylene epoxidation catalyst may be contacted with the conditioning feed gas for a period of time longer than 200 hours, it is believed that this generally does not provide any additional benefit and is not economically attractive as the catalyst does not produce any ethylene oxide during this time.

In those embodiments where an ethylene epoxidation catalyst is contacted with a conditioning feed gas at a temperature that is within a lower portion of the given temperature range, it may be desirable to conduct the conditioning methods for a period of time that is within the upper portion of the given time range. For example, if an ethylene epoxidation catalyst is contacted with a conditioning feed gas at a temperature of from above 180° C. to at most 220° C., or from at least 185° C. to at most 220° C., the period of time where the ethylene epoxidation catalyst is contacted with the conditioning feed gas may be from 6 to 72 hours, or from 6 to 48 hours, or from 6 to 24 hours, or from 12 to 72 hours, or from 12 to 48 hours, or from 12 to 36 hours, or from 12 to 24 hours, or from 24 to 72 hours, or from 24 to 48 hours. Likewise, if an ethylene epoxidation catalyst is contacted with a conditioning feed gas at a temperature that is within an upper portion of the given temperature range, it may be desirable to conduct the conditioning methods for a period of time that is within the lower portion of the given time range. For example, if an ethylene epoxidation catalyst is contacted with a conditioning feed gas at a temperature of from at least 220° C. to at most 250° C., or from at least 220° C. to at most 245° C., the period of time where the ethylene epoxidation catalyst is contacted with the conditioning feed gas may be from 2 to 72 hours, or from 2 to 48 hours, or from 2 to 36 hours, or from 2 to 24 hours, or from 2 to 12 hours, or from 6 to 72 hours, or from 6 to 48 hours, or from 6 to 36 hours, or from 6 to 24 hours, or from 6 to 12 hours.

During the period of time of at least 2 hours when an ethylene epoxidation catalyst is contacted with a conditioning feed gas in the absence of ethylene, the temperature may be maintained at a single temperature or at a plurality of temperatures that are in the range of above 180° C. and at most 250° C. The temperature and/or flow rate of the coolant may be adjusted as necessary to maintain a temperature that is above 180° C. and at most 250° C. throughout this period of time. Optionally, throughout all or part of the period of time when the ethylene epoxidation catalyst is contacted with the conditioning feed gas, the temperature may be progressively increased toward a temperature suitable for epoxidation such as by using a ramp function, a series of steps, or by non-linearly increasing the temperature to a maximum that is at most 250° C. The temperature may be manipulated manually or automatically with a coolant (heating) circuit temperature controller, as is known to those of skill in the art.

The conditioning feed gas employed in the present disclosure comprises oxygen and an inert gas, such as nitrogen, methane, argon, helium, or a combination thereof. Suitably, the conditioning feed gas does not contain ethylene. Optionally, the conditioning feed gas may further comprise an organic chloride, water vapor, carbon dioxide, or a combination thereof.

Oxygen may be provided in any suitable form, such as in its substantially pure molecular form or in a mixture, such as air. Typically, the oxygen concentration in the conditioning feed gas is at least 0.1 mole-%, relative to the total conditioning feed gas, or at least 0.5 mole-%, or at least 1 mole-%, or at least 2 mole-%, or at least 3 mole-%, or at least 4 mole-%, or at least 5 mole-%, on the same basis. Similarly, the oxygen concentration of the conditioning feed gas is typically at most 30 mole-%, relative to the total conditioning feed gas, or at most 21 mole-%, or at most 15 mole-%, or at most 12 mole-%, or at most 10 mole-%, on the same basis. In some embodiments, oxygen may be present in the conditioning feed gas in a concentration of from 0.1 mole-% to 30 mole-%, relative to the total conditioning feed gas, or from 0.1 mole-% to 21 mole-%, or from 0.1 mole-% to 15 mole-%, or from 0.1 mole-% to 10 mole-%, or from 0.1 mole-% to 5 mole-%, or from 0.5 mole-% to 21 mole-%, or from 0.5 mole-% to 15 mole-%, or from 0.5 mole-% to 10 mole-%, or from 0.5 mole-% to 5 mole-%, or from 1 mole-% to 30 mole-%, or from 1 mole-% to 21 mole-%, or from 1 mole-% to 15 mole-%, or from 1 mole-% to 10 mole-%, or from 1 mole-% to 5 mole-%, or from 5 mole-% to 21 mole-%, or from 5 mole-% to 15 mole-%, on the same basis.

Inert gas is generally present in the conditioning feed gas in a concentration of at least 70 mole-%, relative to the total conditioning feed gas, or at least 75 mole-%, or at least 80 mole-%, or at least 85 mole-%, or at least 90 mole-%, or at least 95 mole-%, on the same basis. Similarly, inert gas is typically present in the conditioning feed gas in a concentration of at most 99.9 mole-%, relative to the total conditioning feed gas, or at most 99.5 mole-%, or at most 99 mole-%, or at most 98 mole-%, or at most 95 mole-%, on the same basis. Further, inert gas may be present in the conditioning feed gas in a concentration of from 70 mole-% to 99.9 mole-%, relative to the total conditioning feed gas, of from 70 mole-% to 99.5 mole-%, of from 70 mole-% to 95 mole-%, or from 80 mole-% to 98 mole-%, or from 80 mole-% to 95 mole-%, on the same basis.

Optionally, the conditioning feed gas may further comprise an organic chloride. Examples of organic chlorides suitable for use in the present disclosure include chlorohydrocarbons having from one to eight carbon atoms. Examples of these include, but are not necessarily limited to, methyl chloride, ethyl chloride, ethylene dichloride, vinyl chloride, and a combination thereof. When used, the organic chloride is typically present in the conditioning feed gas in a concentration of 0.1 parts per million by volume (ppmv) or greater, relative to the total conditioning feed gas, or 0.3 ppmv or greater, or 0.5 ppmv or greater, or 1 ppmv or greater, or 2 ppmv or greater, on the same basis. Similarly, when used, the organic chloride is typically present in the conditioning feed gas in a concentration of at most 25 ppmv, relative to the total conditioning feed gas, or at most 22 ppmv, or at most 20 ppmv, or at most 15 ppmv, or at most 10 ppmv, or at most 5 ppmv, on the same basis. Optionally, an organic chloride may be present in the conditioning feed gas in a concentration of from 0.1 to 25 ppmv, relative to the total conditioning feed gas, 0.1 to 20 ppmv, 0.1 to 10 ppmv, 0.1 to 5 ppmv, on the same basis.

The order and manner in which the components of the conditioning feed gas are combined prior to contacting the ethylene epoxidation catalyst is not limited, and they may be combined simultaneously or sequentially. However, as will be recognized by one skilled in the art, it may be desirable to add oxygen to the conditioning feed gas simultaneously with or after the addition of an inert gas for safety reasons. Similarly, the concentration of various components present in the conditioning feed gas (e.g., oxygen, inert gas, organic chloride, etc.) may be maintained at a single concentration or adjusted within the above given concentration ranges throughout the conditioning process.

During the period of time of at least 2 hours when an ethylene epoxidation catalyst is contacted with a conditioning feed gas in the absence of ethylene, the reactor inlet pressure is typically at most 4000 kPa absolute, or at most 3500 kPa absolute, or at most 3000 kPa absolute, or at most 2500 kPa absolute. The reactor inlet pressure is typically at least 500 kPa absolute. The gas flow through the epoxidation reactor is expressed in terms of the Gas Hourly Space Velocity ("GHSV"), which is the quotient of the volumetric flow rate of the feed gas at standard temperature and pressure (i.e., 0° C., 1 atm) divided by the catalyst bed volume (i.e., the volume of the epoxidation reactor that contains ethylene epoxidation catalyst). GHSV represents how many times per hour the feed gas would displace the volume of the epoxidation reactor if the gas were at standard temperature and pressure (i.e., 0° C., 1 atm). When the methods disclosed herein are practiced as a gas phase process involving a packed catalyst bed, the GHSV during conditioning is preferably in the range of from 200 to 10000 Nl/(1·h). However, the conditioning methods disclosed herein are not limited to any particular GHSV and optionally, may be performed where there is no gas flow in the epoxidation reactor, that is to say, where the epoxidation reactor is pressurized with the conditioning feed gas.

After conditioning the epoxidation catalyst in accordance with the methods described herein, the epoxidation process is typically started-up by contacting the ethylene epoxidation catalyst with a start-up feed gas comprising ethylene and oxygen. Optionally, a start-up feed gas may further comprise an organic chloride, carbon dioxide, water vapor, an inert gas, or any combination thereof.

Typically, the ethylene concentration in the start-up feed gas is at least 5 mole-%, relative to the total start-up feed gas, or at least 10 mole-%, or at least 15 mole-%, or at least 20 mole-%, on the same basis. Similarly, the ethylene concentration in the start-up feed gas is typically at most 50 mole-%, relative to the total start-up feed gas, or at most 45 mole-%, or at most 30 mole-%, or at most 25 mole-%, or at most 20 mole-%, on the same basis. In some embodiments, ethylene may be present in the start-up feed gas in a concentration of from 5 mole-% to 50 mole-%, relative to the total start-up feed gas, or from 5 mole-% to 45 mole-%, or from 5 mole-% to 30 mole-%, or from 5 mole-% to 25 mole-%, or from 10 mole-% to 50 mole-%, or from 10 mole-% to 45 mole-%, or from 10 mole-% to 30 mole-%, or from 10 mole-% to 25 mole-%, on the same basis.

The oxygen concentration in the start-up feed gas is typically at least 0.5 mole-%, relative to the total start-up feed gas, or at least 1 mole-%, or at least 2 mole-%, or at least 2.5 mole-%, or at least 5 mole-%, on the same basis. Similarly, the oxygen concentration in the start-up feed gas is typically at most 15 mole-%, relative to the total start-up feed gas, or at most 12 mole-%, or at most 10 mole-%, or at most 5 mole-%, on the same basis. In some embodiments, oxygen may be present in the start-up feed gas in a concentration of from 0.1 mole-% to 15 mole-%, relative to the total start-up feed gas, or from 1 mole-% to 12 mole-%, or from 1 mole-% to 10 mole-%, or from 2 mole-% to 10 mole-%, on the same basis. It may be advantageous for the start-up feed gas to have a lower oxygen concentration than the epoxidation feed gas utilized during normal ethylene oxide production, because a lower oxygen concentration in the start-up feed gas will reduce the oxygen conversion level so that, advantageously, hot spots in the catalyst bed are better avoided and the process will be more easily controllable. However, as previously mentioned, an ethylene epoxidation catalyst conditioned in accordance with the conditioning methods of the present disclosure may advantageously exhibit a lower oxygen conversion level at the point when the start-up feed gas is first introduced than the same epoxidation catalyst would otherwise demonstrate. Therefore, it is also possible that the oxygen concentration in the start-up feed gas and/or the oxygen feed rate can be increased at a faster rate, which can significantly reduce the amount of time that is required before an oxygen concentration is achieved that is comparable to that utilized during normal ethylene oxide production.

Optionally, the start-up feed gas may further comprise an organic chloride. Examples of organic chlorides suitable for use in the present disclosure include chlorohydrocarbons having from one to eight carbon atoms. Examples of these include, but are not necessarily limited to, methyl chloride, ethyl chloride, ethylene dichloride, vinyl chloride, and a combination thereof. When used, the organic chloride is typically present in the start-up feed gas in a concentration of 0.1 ppmv or greater, relative to the total start-up feed gas, or 0.3 ppmv or greater, or 0.5 ppmv or greater, on the same basis. Similarly, when used, the organic chloride concentration in the start-up feed gas is typically at most 25 ppmv, relative to the total start-up feed gas, or at most 22 ppmv, or at most 20 ppmv, on the same basis. Optionally, the organic chloride concentration in the start-up feed gas may be from 0.1 to 25 ppmv, relative to the total start-up feed gas, or from 0.3 to 20 ppmv, on the same basis. Typically, as the feed gas composition changes and/or as one or more of the operating conditions change, the concentration of organic chloride in the start-up feed gas may also be adjusted so as to maintain the optimum concentration. For additional disclosure regarding optimization of organic chloride, reference may be made to, for example U.S. Pat. Nos. 7,193,094 and 7,485,597, which are incorporated herein by reference.

Optionally, the start-up feed gas may be substantially free, and preferably completely free, of a nitrogen-containing reaction modifier. That is to say, the start-up feed gas may comprise less than 100 ppm of a nitrogen-containing reaction modifier, preferably less than 10 ppm, more preferably less than 1 ppm, and most preferably 0 ppm of a nitrogen-containing reaction modifier. As used herein, the term "nitrogen-containing reaction modifier" refers to a gaseous compound or volatile liquid that is present as, or capable of forming, nitrogen oxides in oxidizing conditions. Examples of nitrogen-containing reaction modifiers include, but are not limited to, NO, NO2, N2O3, N2O4, N2O5 or any substance capable of forming one of the aforementioned gases under epoxidation conditions (e.g., hydrazine, hydroxylamine, ammonia, organic nitro compounds (such as nitromethane, nitroethane, nitrobenzene, etc), amines, amides, organic nitrites (such as methyl nitrite), nitriles (such as acetonitrile)), and a combination thereof.

Optionally, the start-up feed gas may further comprise carbon dioxide. When used, carbon dioxide is typically present in the start-up feed gas in a concentration of at most 6 mole-%, relative to the total start-up feed gas, or at most 4 mole-%, or at most 3 mole-%, or at most 2 mole-%, or at most 1 mole-%, on the same basis. Similarly, when used, the carbon dioxide concentration in the start-up feed gas is typically at least 0.1 mole-%, relative to the total start-up feed gas, or at least 0.2 mole-%, or at least 0.3 mole-%, or at least 0.5 mole-%, or at least 1 mole-%, on the same basis. In some embodiments, carbon dioxide may be present in the start-up feed gas in a concentration of from 0.1 mole-% to 6 mole-%, relative to the total start-up feed gas, or from 0.1 mole-% to 4 mole-%, or from 0.1 mole-% to 3 mole-%, or from 0.1 mole-% to 2 mole-%, on the same basis. Suitably, carbon dioxide may be present in the start-up feed gas in the same or substantially the same concentration as in the epoxidation feed gas utilized during normal ethylene oxide production.

Typically, the ethylene epoxidation catalyst is initially contacted with a start-up feed gas comprising ethylene and oxygen at a temperature that is above 180° C. and at most 250° C. After a period of time, the ethylene epoxidation reaction will begin producing heat, further increasing the temperature. During the period of time when the ethylene epoxidation catalyst is contacted with the start-up feed gas, the temperature may be maintained at a single temperature or at a plurality of temperatures that are in the range of from above 180° C. to at most 320° C., or from at least 185° C. to at most 300° C., or from at least 185° C. to at most 280° C., or from at least 220° C. to at most 300° C., or at least 220° C. to at most 280° C., or from at least 230° C. to at most 280° C. As those of ordinary skill in the chemical engineering art are aware, there are many suitable ways for adjusting the temperature within a chemical process, including, but not limited to, temperature, flow rate, and pressure of the coolant; feed gas composition, space velocity, and reactor inlet pressure, etc., and any of these may be utilized as necessary to adjust and/or maintain the temperature of the present process.

During the period of time when the ethylene epoxidation catalyst is contacted with the start-up feed gas, the reactor inlet pressure is typically at most 4000 kPa absolute, or at most 3500 kPa absolute, or at most 3000 kPa absolute, or at most 2500 kPa absolute. The reactor inlet pressure is typically at least 500 kPa absolute. Preferably, when the methods disclosed herein are practiced as a gas phase process involving a packed catalyst bed, the GHSV during start-up is in the range of from 500 to 10000 Nl/(l·h).

The order and manner in which the components of the start-up feed gas are combined prior to contacting the ethylene epoxidation catalyst is not limited, and they may be combined simultaneously or sequentially. The order and manner in which the components of the start-up feed gas are combined may be chosen for convenience and/or for safety reasons. Furthermore, as will be recognized by one of skill in the art, the concentration of various components present in the start-up feed gas (e.g., ethylene, oxygen, inert gas, organic chloride, etc.) may be maintained at a single concentration or adjusted within the above given concentration ranges throughout start-up. For example, throughout all or part of the period of time when the ethylene epoxidation catalyst is contacted with a start-up feed gas, the concentration of various components present in the start-up feed gas (e.g., ethylene, oxygen, inert gas, organic chloride, etc.) may be may be progressively increased (or decreased) toward a concentration that is the same or substantially the same concentration as in the epoxidation feed gas utilized during normal ethylene oxide production.

Optionally, after conditioning an ethylene epoxidation catalyst in accordance with the methods described herein, the epoxidation catalyst may be subjected to a heat treatment any time after introduction of the start-up feed gas. For example, the epoxidation catalyst may be brought up to a temperature that is above 250° C. and typically at most 320° C., and contacted with a feed gas comprising oxygen and ethylene. Further details on suitable heat treatments may be found, for example, in U.S. Pat. Nos. 7,102,022 and 7,485,597, which are incorporated herein by reference.

A further description of epoxidation catalysts employed in the present disclosure will now be provided. Epoxidation catalysts suitable for use in the methods described herein are commonly referred to as high selectivity catalysts and comprise a carrier having silver and a rhenium promoter deposited thereon. The carrier (also known as a "support") may be selected from a wide range of materials. Such carrier materials may be natural or artificial inorganic materials and they include silicon carbide, clays, pumice, zeolites, charcoal, and alkaline earth metal carbonates, such as calcium carbonate. Preferred are refractory carrier materials, such as alumina, magnesia, zirconia, silica, and mixtures thereof. The most preferred carrier material is α-alumina. In some embodiments, a carrier may comprise α-alumina in a quantity of at least 80% w, 90% w, or 95% w α-alumina, for example up to 99.9% w, in particular up to 99% w, relative to the weight of the catalyst.

Carriers suitable for use herein may be selected from those having a varied and wide range of physical properties, including shape, size, surface area, water absorption, crush strength, attrition resistance, total pore volume, median pore diameter, pore size distributions, etc.

Suitable shapes for a carrier include any of the wide variety of shapes known for carriers, which include, but are not limited to, pills, chunks, tablets, pieces, pellets, rings, spheres, wagon wheels, trapezoidal bodies, doughnuts, amphora, rings, Raschig rings, honeycombs, monoliths, saddles, cylinders, hollow cylinders, multi-lobed cylinders, cross-partitioned hollow cylinders (e.g., cylinders having at least one partition extending between walls), cylinders having gas channels from side wall to side wall, cylinders having two or more gas channels, and ribbed or finned structures. While the cylinders are often circular, other cross-sections, such as oval, hexagonal, quadrilateral, trilateral, and multi-lobed may be useful. Reference may be made to U.S. Pat. No. 8,871,677 incorporated by reference herein, for further description of multi-lobed carriers.

Additionally, the size of the carrier is generally not limited, and may include any size suitable for use in an epoxidation reactor. For example, a carrier may be in the shape of a cylinder having a length of 5 to 15 millimeters ("mm"), an outside diameter of 5 to 15 mm, and an inside diameter of 0.2 to 4 mm. In some embodiments, the carrier may have a length-to-outside diameter ratio of 0.8 to 1.2. Additionally, the carrier may be in the shape of a hollow cylinder with a wall thickness of 1 to 7 mm. It is within the ability of one skilled in the art, with the benefit of this disclosure, to select a suitable shape and size of a carrier, taking into consideration, for example, the type and configuration of the epoxidation reactor in which the carrier will be employed (e.g., the length and internal diameter of the tubes within the epoxidation reactor).

In general, the surface area of a carrier is indicative of the amount of surface area per gram of carrier that is available for the deposition of catalytic material (e.g., silver). The surface area of a carrier suitable for use herein is not narrowly critical and may be, for example, from 0.1 to 10 m2/g, relative to the weight of the carrier, or from 0.5 to 5 m2/g, or from 0.7 to 3 m2/g, or at least 0.1 m2/g, or at least 0.3 m2/g, or at least 0.5 m2/g, or at least 0.6 m2/g, or at most 10 m2/g, or at most 5 m2/g, or at most 3 m2/g, on the same basis. As used herein, "surface area" is understood to refer to the surface area of the carrier as measured in accordance with the B.E.T. (Brunauer, Emmett and Teller) method as described in detail in Brunauer, S., Emmet, P. Y. and Teller, E., J. Am. Chem. Soc., 60, 309-16 (1938).

The water absorption of a carrier is typically expressed as the weight of water than can be absorbed into the pores of the carrier, relative to the weight of the carrier, and therefore reported as grams of water per gram of carrier and the units may be abbreviated as "g/g". Typically, the water absorption of a carrier suitable for use herein may be, for example, from 0.2 to 1.2 g/g, relative to the weight of the carrier, or at least 0.2 g/g, or at least 0.25 g/g, or at least 0.3 g/g, or at most 0.8 g/g, or at most 0.75 g/g, or at most 0.7 g/g, on the same basis. As used herein, the term "water absorption" is understood to refer to the water absorption of a carrier as measured in accordance with the following procedure: First, approximately 100 g of representative samples of carrier are dried at 110° C. for a minimum of one hour. The samples are then cooled in a desiccator and the dry weight (D) of each sample is then determined to the nearest 0.01 g. The samples are then placed in a pan of distilled water and boiled for thirty minutes. While the water is boiling, the samples are covered with water and setter pins or some similar device are used to separate the samples from the bottom and sides of the pan and from each other. After the thirty minute boil, the samples are transferred to room temperature water and allowed to soak for an additional fifteen minutes. After returning to room temperature, each sample is then blotted lightly with a moistened, lint-free linen or cotton cloth to remove all excess water from the surface and the saturated weight (M) of each sample is determined to the nearest 0.01 g. The blotting operation may be accomplished by rolling the specimen lightly on the wet cloth which shall previously have been saturated with water and then pressed only enough to remove such water as will drip from the cloth. Excessive blotting should be avoided because it will introduce error by withdrawing water from the pores of the sample. The samples should be weighed immediately after blotting. The entire operation should be completed as quickly as possible to minimize errors caused by evaporation of water from the sample. Water absorption (A) is expressed as the weight of water absorbed, relative to the weight of the dried carrier and is determined using the following formula: $A=[(M-D)/D]$ wherein the water absorption is expressed in units of grams of water per gram of carrier ("g/g"). Water absorption may also be expressed in units of "cc/g", provided there is a correction for the density of water at the conditions measured. Alternatively, when water absorption is measured according to the above described procedure, it may be convenient to express the water absorption in units of grams of water absorbed per 100 grams of carrier (e.g., 60 g/100 g), which may also be expressed as the weight percentage of water absorbed per 100 g of carrier (e.g., 60%). The water absorption of a carrier may be positively correlated to and thus used interchangeably with the term "porosity" which, in the field of catalyst carriers, is usually understood to mean the carrier's open cell porosity. Generally, as the water absorption of a carrier increases, the ease of deposition of catalytic material on the carrier increases. However, at higher water absorptions, the carrier, or an epoxidation catalyst comprising the carrier, may have lower crush strength or attrition resistance.

The crush strength of a carrier is typically expressed as the amount of compressive force required to crush the carrier, relative to the length of the carrier, and therefore reported as the amount of force per millimeter of carrier and the units may be abbreviated as "N/mm". The crush strength of a carrier suitable for use herein is not narrowly critical, although it should have a crush strength sufficient to allow for its use in the commercial production of ethylene oxide. Typically, the crush strength of a carrier suitable for use herein may be, for example, at least 1.8 N/mm, or at least 2 N/mm, or at least 3.5 N/mm, or at least 5 N/mm and frequently as much as 40 N/mm, or as much as 25 N/mm, or as much as 15 N/mm. As used herein, the term "crush strength" is understood to refer to the crush strength of a carrier as measured in accordance with ASTM D6175-03, wherein the test sample is tested as such after its preparation, that is with elimination of Step 7.2 of said method, which represents a step of drying the test sample. For this crush strength test method, the crush strength of the carrier is typically measured as the crush strength of hollow cylindrical particles of 8.8 mm external diameter, 3.5 mm internal diameter, and 8 mm length.

In general, the attrition resistance of a carrier is indicative of the propensity of the carrier to produce fines in the course of transportation, handing and use. The attrition resistance of a carrier suitable for use herein is not narrowly critical, although it should be sufficiently robust so to allow for its use in the commercial production of ethylene oxide. Typically, a carrier suitable for use herein may exhibit an attrition of at most 50%, or at most 40%, or at most 30% and is typically at least 5%, or at least 10%, or at least 15%, or at least 20%. As used herein, "attrition resistance" is understood to refer to the attrition resistance of a carrier as measured in accordance with ASTM D4058-92, wherein the test sample is tested as such after its preparation, that is with elimination of Step 6.4 of the said method, which represents a step of drying the test sample. For this test method, the attrition resistance of the carrier is typically measured as the attrition resistance of hollow cylindrical particles of 8.8 mm external diameter, 3.5 mm internal diameter, and 8 mm length.

The total pore volume, the median pore diameter, and the pore size distribution of a carrier may be measured by a conventional mercury intrusion porosimetry device in which liquid mercury is forced into the pores of a carrier. Greater pressure is needed to force the mercury into the smaller pores and the measurement of pressure increments corresponds to volume increments in the pores penetrated and hence to the size of the pores in the incremental volume. As used herein, the pore size distribution, the median pore diameter and the pore volumes are as measured by mercury intrusion porosimetry to a pressure of $2.1 \times 10^8$ Pa using a Micromeritics Autopore 9200 model (130° contact angle, mercury with a surface tension of 0.480 N/m, and correction for mercury compression applied). As used herein, the median pore diameter is understood to mean the pore diameter corresponding to the point in the pore size distribution at which 50% of the total pore volume is found in pores having less than (or greater than) said point.

The total pore volume of a carrier suitable for use herein is not narrowly critical and may be, for example, at least 0.20 mL/g, at least 0.30 mL/g, at least 0.40 mL/g, at least 0.50 mL/g and is typically at most 0.80 mL/g, at most 0.75 mL/g, or at most 0.70 mL/g. Generally, as the total pore volume of a carrier increases, the ability to deposit catalytic material on the carrier increases. However, at higher total pore volumes, the carrier, or an epoxidation catalyst comprising the carrier, may have lower crush strength or attrition resistance. The median pore diameter of a carrier suitable for use herein is not narrowly critical and may be, for example, from 0.50 to 50 μm. In addition, a carrier suitable for use herein may have a pore size distribution that is monomodal, bimodal or multimodal.

In addition to the carrier, ethylene epoxidation catalysts suitable for use in the present disclosure comprise silver and a rhenium promoter deposited thereon. Optionally, an ethylene epoxidation catalyst may further comprise one or more of an alkali metal promoter (e.g., lithium, sodium, potassium, rubidium, cesium, and a combination thereof), a co-promoter (e.g., sulfur, phosphorus, boron, tungsten, molybdenum, chromium, and a combination thereof), a further metal promoter (e.g., alkaline earth metal (such as beryllium, magnesium, calcium, strontium, barium, etc.), titanium, hafnium, zirconium, vanadium, thallium, thorium, tantalum, niobium, gallium, germanium and a combination thereof), and/or a combination thereof.

In broad terms, silver is deposited onto a carrier in an amount sufficient to catalyze the vapor phase reaction of ethylene with oxygen to produce ethylene oxide. When ethylene epoxidation catalysts comprising different amounts of silver are prepared on carriers of similar packing densities, it is convenient to compare the epoxidation catalysts on a silver weight basis, which is typically expressed in weight percent silver as a function of the total weight of the epoxidation catalyst. As used herein, unless otherwise specified, the total weight of the epoxidation catalyst is understood to refer to the weight of the carrier and all components deposited thereon, including silver, rhenium promoter, and any optional promoter(s). Typically, epoxidation catalysts suitable for use herein comprise silver in an amount of 1% to 55% by weight, relative to the total weight of the epoxidation catalyst, or from 1% to 50% by weight, or from 5% to 40% by weight, or from 8% to 35% by weight, or from 10% to 30% by weight, or at least 10% by weight, or at least 15% by weight, or at most 45% by weight, or at most 40% by weight, on the same basis. The upper and lower limits of suitable amounts of silver can be suitably varied, depending upon the particular catalytic performance characteristics or effect desired or the other variables involved, including economic factors.

Alternatively, the amount of silver included in an ethylene epoxidation catalyst can be expressed in terms of mass of silver per unit volume of epoxidation catalyst loaded into an epoxidation reactor (e.g., into the catalyst bed). In this way, comparisons of silver loadings between epoxidation catalysts prepared on carriers of different packing densities can be made. Ultimately, the catalyst bed contains a defined volume of epoxidation catalyst, so this method of comparing the amount of silver deposited on an epoxidation catalyst is appropriate. Accordingly, epoxidation catalysts suitable for use herein may comprise silver in an amount of at least 50 kg/m3, relative to the total volume of epoxidation catalyst loaded into the catalyst bed, or at least 100 kg/m3, or at least 125 kg/m3, or at least 150 kg/m3, on the same basis. Similarly, epoxidation catalysts suitable for use herein may comprise silver in an amount of at most 500 kg/m3, relative to the total volume of epoxidation catalyst loaded into the catalyst bed, or at most 450 kg/m3, or at most 400 kg/m3, or at most 350 kg/m3, on the same basis. Preferably, epoxidation catalysts comprise silver in an amount of from 50 to 500 kg/m3, relative to the total volume of epoxidation catalyst loaded into the catalyst bed, or from 100 to 450 kg/m3, or from 125 to 350 kg/m3, on the same basis.

Epoxidation catalysts suitable for use herein may comprise a rhenium promoter deposited on a carrier in an amount of 0.01 to 50 mmole/kg, calculated as the amount of rhenium relative to the total weight of the epoxidation catalyst, or from 0.1 to 50 mmole/kg, or from 0.1 to 25 mmole/kg, or from 0.1 to 20 mmole/kg, or from 0.5 to 10 mmole/kg, or from 1 to 6 mmole/kg, or at least 0.01 mmole/kg, or at least 0.1 mmole/kg, or at least 0.5 mmole/kg, or at least 1 mmole/kg, or at least 1.25 mmole/kg, or at least 1.5 mmole/kg, or at most 50 mmole/kg, or at most 20 mmole/kg, or at most 10 mmole/kg, or at most 6 mmole/kg, on the same basis. Alternatively stated, the amount of rhenium promoter, expressed relative to the surface area of the carrier, may preferably be present in the epoxidation catalyst in an amount of from 0.25 to 10 μmole/m2, or from 0.5 to 5 μmole/m2, or from 1 to 3 μmole/m2. For purposes of convenience, the amount of rhenium promoter deposited on the epoxidation catalyst is measured as the metal, irrespective of the form in which it is present.

Optionally, epoxidation catalysts suitable for use herein may further comprise an alkali metal promoter (e.g., lithium, sodium, potassium, rubidium, cesium, or a combination thereof) deposited on a carrier in an amount of 0.01 to 500 mmole/kg, calculated as the amount of the element relative to the total weight of the epoxidation catalyst, or from 0.01 to 400 mmole/kg, or from 0.1 to 300 mmole/kg, or from 0.1 to 250 mmole/kg, or from 0.5 to 200 mmole/kg, or from 1 to 100 mmole/kg, or at least 0.01 mmole/kg, or at least 0.05, or at least 0.1 mmole/kg, or at least 0.5 mmole/kg, or at least 1 mmole/kg, or at least 1.25 mmole/kg, or at least 1.5 mmole/kg, or at least 2 mmole/kg, or at least 3 mmole/kg, or at most 500 mmole/kg, or at most 400 mmole/kg, or at most 300 mmole/kg, or at most 250 mmole/kg, or at most 200 mmole/kg, or at most 150 mmole/kg, or at most 100 mmole/kg, on the same basis. For purposes of convenience, the amount of the alkali metal deposited on the epoxidation catalyst is measured as the element, irrespective of the form in which it is present.

It should be understood that the amount of an alkali metal promoter deposited on the carrier is not necessarily the total amount of alkali metal present in the epoxidation catalyst. Rather, the amount deposited reflects the amount of alkali metal promoter that has been added to the carrier (e.g., via impregnation). As such, the amount of alkali metal promoter deposited on the carrier does not include any amount of alkali metals that may be locked into the carrier, for example, by calcining, or are not extractable in a suitable solvent such as water or lower alkanol or amine or mixtures thereof and do not provide a promoting effect. It is also understood that the source of the alkali metal promoter may be the carrier itself. That is, the carrier may contain extractable amounts of an alkali metal promoter that can be extracted with a suitable solvent, such as water or lower alkanol, thus preparing a solution from which the alkali metal promoter may be deposited or redeposited on the carrier.

In those embodiments where an ethylene epoxidation catalyst comprises an alkali metal promoter, it may be beneficial if the catalyst comprises a combination of two or more alkali metal promoters. Non-limiting examples include a combination of cesium and rubidium, a combination of cesium and potassium, a combination of cesium and sodium, a combination of cesium and lithium, a combination of cesium, rubidium and sodium, a combination of cesium, potassium and sodium, a combination of cesium, lithium and sodium, a combination of cesium, rubidium and sodium, a combination of cesium, rubidium, potassium and lithium, and a combination of cesium, potassium, and lithium.

Optionally, epoxidation catalysts suitable for use herein may further comprise a co-promoter (e.g., sulfur, phosphorus, boron, tungsten, molybdenum, chromium, or a combination thereof) deposited on a carrier in an amount of 0.01 to 500 mmole/kg, calculated as the amount of the element relative to the total weight of the epoxidation catalyst, or from 0.01 to 100 mmole/kg, or from 0.1 to 50 mmole/kg, or from 0.1 to 20 mmole/kg, or from 0.5 to 10 mmole/kg, or from 1 to 6 mmole/kg, or at least 0.01 mmole/kg, or at least 0.05, or at least 0.1 mmole/kg, or at least 0.5 mmole/kg, or at least 1 mmole/kg, or at least 1.25 mmole/kg, or at least 1.5 mmole/kg, or at least 2 mmole/kg, or at least 3 mmole/kg, or at most 100 mmole/kg, or at most 50 mmole/kg, or at most 40 mmole/kg, or at most 30 mmole/kg, or at most 20 mmole/kg, or at most 10 mmole/kg, or at most 5 mmole/kg, on the same basis. For purposes of convenience, the amount of co-promoter deposited on the epoxidation catalyst is measured as the element, irrespective of the form in which it is present.

In those embodiments where an ethylene epoxidation catalyst comprises a co-promoter, it may be particularly beneficial if the co-promoter comprises a combination of a first co-promoter selected from sulfur, phosphorus, boron, and a combination thereof, and a second co-promoter selected from the group consisting of tungsten, molybdenum, chromium, and a combination thereof. The amount of the first co-promoter deposited on the carrier may be in an amount of 0.2 to 50 mmole/kg, calculated as the amount of the element (e.g., sulfur, phosphorus and/or boron) relative to the total weight of the epoxidation catalyst, or from 0.5 to 45 mmole/kg, or from 0.5 to 30 mmole/kg, or from 1 to 20 mmole/kg, or from 1.5 to 10 mmole/kg, or from 2 to 6 mmole/kg, or at least 0.2 mmole/kg, or at least 0.3, or at least 0.5 mmole/kg, or at least 1 mmole/kg, or at least 1.25 mmole/kg, or at least 1.5 mmole/kg, or at least 1.75 mmole/kg, or at least 2 mmole/kg, or at least 3 mmole/kg, or at most 50 mmole/kg, or at most 45 mmole/kg, or at most 40 mmole/kg, or at most 35 mmole/kg, or at most 30 mmole/kg, or at most 20 mmole/kg, or at most 10 mmole/kg, or at most 6 mmole/kg, on the same basis. The amount of the second co-promoter deposited on the carrier may be in an amount of 0.1 to 40 mmole/kg, calculated as the amount of the element (e.g., tungsten, molybdenum and/or chromium) relative to the total weight of the epoxidation catalyst, or from 0.15 to 30 mmole/kg, or from 0.2 to 25 mmole/kg, or from 0.25 to 20 mmole/kg, or from 0.3 to 10 mmole/kg, or from 0.4 mmole/kg to 5 mmole/kg, or at least 0.1 mmole/kg, or at least 0.15, or at least 0.2 mmole/kg, or at least 0.25 mmole/kg, or at least 0.3 mmole/kg, or at least 0.35 mmole/kg, or at least 0.4 mmole/kg, or at least 0.45 mmole/kg, or at least 0.5 mmole/kg, or at most 40 mmole/kg, or at most 35 mmole/kg, or at most 30 mmole/kg, or at most 25 mmole/kg, or at most 20 mmole/kg, or at most 15 mmole/kg, or at most 10 mmole/kg, or at most 5 mmole/kg, on the same basis. Further, it may be beneficial to deposit the first and second co-promoters in an amount such that the molar ratio of the first co-promoter to the second co-promoter is greater than 1, or at least 1.25, at least 1.5, at least 2, or at least 2.5. It is further preferred that the molar ratio of the first co-promoter to the second co-promoter is at most 20, at most 15, at most 10, or at most 7.5. Additionally, it is preferred that the molar ratio of the rhenium promoter to the second co-promoter may be greater than 1, at least 1.25, or at least 1.5. It is further preferred that the molar ratio of the rhenium promoter to the second co-promoter may be at most 20, at most 15, or at most 10.

Optionally, epoxidation catalysts suitable for use herein may additionally comprise a further metal promoter (e.g., an alkaline earth metal such as beryllium, magnesium, calcium, strontium, barium, etc., titanium, hafnium, zirconium, vanadium, thallium, thorium, tantalum, niobium, gallium, germanium, manganese, etc.) deposited on a carrier in an amount of 0.01 to 500 mmole/kg, calculated as the amount of the element relative to the total weight of the epoxidation catalyst, or from 0.01 to 100 mmole/kg, or from 0.1 to 50 mmole/kg, or from 0.1 to 20 mmole/kg, or from 0.5 to 10 mmole/kg, or from 1 to 6 mmole/kg, or at least 0.01 mmole/kg, or at least 0.05, or at least 0.1 mmole/kg, or at least 0.5 mmole/kg, or at least 1 mmole/kg, or at least 1.25 mmole/kg, or at least 1.5 mmole/kg, or at least 2 mmole/kg, or at least 3 mmole/kg, or at most 100 mmole/kg, or at most 50 mmole/kg, or at most 40 mmole/kg, or at most 30 mmole/kg, or at most 20 mmole/kg, or at most 10 mmole/kg, or at most 5 mmole/kg, on the same basis. For purposes of convenience, the amount of further metal promoter in the epoxidation catalyst is measured as the element, irrespective of the form in which it is present.

The degree of benefit obtained within the above-defined concentration limits for a rhenium promoter and/or any optional promoter(s) can vary depending upon one or more properties and characteristics, such as, for example, epoxidation conditions, catalyst preparative conditions, the physical properties and surface chemical properties of the carrier utilized, the amount of silver deposited on the epoxidation catalyst, the amount of rhenium promoter deposited on the epoxidation catalyst, the amount (if any) of optional promoter(s) deposited on the epoxidation catalyst, and the amount of other cations and anions present in the epoxidation catalyst, either alone or in combination with the rhenium promoter and/or optional promoter(s). Accordingly, the above-defined limits were selected to cover the widest possible variations in properties and characteristics.

Well known methods can be employed to analyze for the amounts of silver, rhenium promoter, and optional promoter(s) deposited onto the carrier. The skilled artisan may employ, for example, material balances to determine the amounts of any of these deposited components. As an example, if the carrier is weighed prior to and after deposition of silver and a rhenium promoter, then the difference in the two weights will be equal to the amount of silver and the rhenium promoter deposited onto the carrier, from which the amount of the deposited rhenium promoter can be calculated. Additionally, the amount of the deposited silver and promoters can be calculated based upon the ratio of the concentration of silver and promoters included in the impregnation solution(s) and the total weight in the finished epoxidation catalyst. Alternatively, the amount of promoters deposited on the carrier may also be determined by known leaching methods, wherein the amount of metallic leachables present in the carrier and the amount of metallic leachables present in the epoxidation catalyst are independently determined and the difference between the two measurements reflect the total amount of promoter deposited on the carrier.

The preparation of ethylene epoxidation catalysts comprising silver is known in the art. The specific manner in which ethylene epoxidation catalysts suitable for use herein are prepared is not limited, and therefore any method known in the art may be used. Reference is made to U.S. Pat. Nos. 4,761,394, 4,766,105, 5,380,697, 5,739,075, 6,368,998 and 6,656,874, which are incorporated herein by reference, for descriptions relating to the preparation of ethylene epoxidation catalysts.

Generally speaking, the ethylene epoxidation processes of the present disclosure may be carried out in a variety of ways known in the art, however, it is preferred to carry out the epoxidation process as a continuous, gas-phase process. The ethylene epoxidation processes may be carried out in any known epoxidation reactor (e.g., any reactor vessel used to react ethylene and oxygen), such as a fixed bed reactor (e.g., a fixed bed tubular reactor), a continuous stirred tank reactor (CSTR), a fluid bed reactor, etc. Additionally, a plurality of epoxidation reactors may be used in parallel.

One commercial example of a suitable epoxidation reactor is a vertical shell-and-tube heat exchanger, wherein the shell contains a coolant (e.g., heat transfer fluid (such as tetralin), water, etc.) to regulate the temperature of the epoxidation reactor and wherein the plurality of tubes are substantially parallel, elongated tubes that contain the ethylene epoxidation catalyst. While the size and number of tubes may vary from reactor to reactor, a typical tube used in a commercial reactor may have a length of from 3 to 25 meters, from 5 to 20 meters, or from 6 to 15 meters. Similarly, the reactor tubes may have an internal tube diameter of from 5 to 80 millimeters, from 10 to 75 millimeters, or from 20 to 60 millimeters. The number of tubes present in an epoxidation reactor can vary widely and may range in the thousands, for example up to 22,000, or from 1,000 to 11,000, or from 1,500 to 18,500.

The portion of the epoxidation reactor containing the ethylene epoxidation catalyst (e.g., reactor tubes) is commonly referred to as the "catalyst bed". In general, the amount of ethylene epoxidation catalyst in the catalyst bed, the height of the catalyst bed and the packing density of the epoxidation catalyst within the catalyst bed (i.e., the "tube packing density") may vary over a wide range, depending upon, for example, the size and number of tubes present within the epoxidation reactor and the size and shape of the epoxidation catalyst. However, typical ranges for the tube packing density may be from 400 to 1500 kg/m3. Similarly, typical ranges for catalyst bed height may be from 50% to 100% of the reactor tube length. In those embodiments where the catalyst bed height is less than 100% of the reactor tube length, the remaining portion of the tube may be empty or optionally comprise particles of a non-catalytic or inert material.

In accordance with the methods of the present disclosure, after an ethylene epoxidation catalyst comprising a carrier, having silver and a rhenium promoter deposited thereon, has been contacted with a conditioning feed gas comprising oxygen for a period of time of at least 2 hours at a temperature that is above 180° C. and at most 250° C., in an epoxidation reactor and in the absence of ethylene, the ethylene epoxidation catalyst is contacted with an epoxidation feed gas comprising ethylene, oxygen and an organic chloride. Optionally, the epoxidation feed gas may further comprise carbon dioxide, water vapor, an inert gas, such as nitrogen, methane, ethane, argon, helium, etc., and a combination thereof.

Ethylene may be present in the epoxidation feed gas in a concentration that may vary over a wide range. However, ethylene is typically present in the epoxidation feed gas in a concentration of at least 5 mole-%, relative to the total epoxidation feed gas, or at least 8 mole-%, or at least 10 mole-%, or at least 12 mole-%, or at least 14 mole-%, or at least 20 mole-%, or at least 25 mole-%, on the same basis. Similarly, ethylene is typically present in the epoxidation feed gas in a concentration of at most 65 mole-%, or at most 60 mole-%, or at most 55 mole-%, or at most 50 mole-%, or at most 48 mole-%, on the same basis. In some embodiments, ethylene may be present in the epoxidation feed gas in a concentration of from 5 mole-% to 60 mole-%, relative to the total epoxidation feed gas, or from 10 mole-% to 50 mole-%, or from 12 mole-% to 48 mole-%, on the same basis.

In general, the oxygen concentration in the epoxidation feed gas should be less than the concentration of oxygen that would form a flammable mixture at either the reactor inlet or the reactor outlet at the prevailing operating conditions. Often, in practice, the oxygen concentration in the epoxidation feed gas may be no greater than a pre-defined percentage (e.g., 95%, 90%, etc.) of oxygen that would form a flammable mixture at either the reactor inlet or the reactor outlet at the prevailing operating conditions. Although the oxygen concentration may vary over a wide range, the oxygen concentration in the epoxidation feed gas is typically at least 0.5 mole-%, relative to the total epoxidation feed gas, or at least 1 mole-%, or at least 2 mole-%, or at least 3 mole-%, or at least 4 mole-%, or at least 5 mole-%, on the same basis. Similarly, the oxygen concentration of the epoxidation feed gas is typically at most 20 mole-%, relative to the total epoxidation feed gas, or at most 15 mole-%, or at most 12 mole-%, or at most 10 mole-%, on the same basis. In some embodiments, oxygen may be present in the epoxidation feed gas in a concentration of from 1 mole-% to 15 mole-%, relative to the total epoxidation feed gas, or from 2 mole-% to 12 mole-%, or from 3 mole-% to 10 mole-%, on the same basis. Typically, as the oxygen concentration in the epoxidation feed gas increases, the required temperature decreases. However as previously mentioned, in practice, flammability is generally the limiting factor for the maximum concentration of oxygen in the epoxidation feed gas. Accordingly, in order to remain outside the flammable regime, the oxygen concentration of the epoxidation feed gas may be lowered as the ethylene concentration of the epoxidation feed gas is increased. It is within the ability of one skilled in the art to determine a suitable concentration of oxygen to be included in the epoxidation feed gas, taking into consideration, for example, the overall epoxidation feed gas composition, along with the other operating conditions, such as pressure and temperature.

Typically, the organic chloride concentration in the epoxidation feed gas is at least 0.1 parts per million by volume (ppmv) or greater, relative to the total epoxidation feed gas, or 0.3 ppmv or greater, or 0.5 ppmv or greater, on the same basis. Similarly, the organic chloride concentration in the epoxidation feed gas is typically at most 25 ppmv, relative to the total epoxidation feed gas, or at most 22 ppmv, or at most 20 ppmv, on the same basis. Further, the organic chloride concentration in the epoxidation feed gas may be from 0.1 to 25 ppmv, relative to the total epoxidation feed gas, or from 0.3 to 20 ppmv, on the same basis. Typically, as the epoxidation feed gas composition changes and/or as one or more of the operating conditions change, the concentration of organic chloride in the epoxidation feed gas may also be adjusted so as to maintain the optimum concentration. For additional disclosure regarding optimization of organic chloride, reference may be made to, for example U.S. Pat. Nos. 7,193,094 and 7,485,597, which is incorporated herein by reference.

Optionally, the epoxidation feed gas may be substantially free, and preferably completely free, of a nitrogen-containing reaction modifier. That is to say, the epoxidation feed gas may comprise less than 100 ppm of a nitrogen-containing reaction modifier, preferably less than 10 ppm, more preferably less than 1 ppm, and most preferably 0 ppm of a nitrogen-containing reaction modifier.

Optionally, the epoxidation feed gas may further comprise carbon dioxide. When present, carbon dioxide is typically present in the epoxidation feed gas in a concentration of 0.10 mole-% or greater, relative to the total epoxidation feed gas, or 0.12 mole-% or greater, or 0.15 mole-% or greater, or 0.17 mole-% or greater, or 0.20 mole-% or greater, or 0.22 mole-% or greater, or 0.25 mole-% or greater, on the same basis. Similarly, carbon dioxide is generally present in the epoxidation feed gas in a concentration of at most 10 mole-%, relative to the total epoxidation feed gas, or at most 8 mole-%, or at most 5 mole-%, or at most 3 mole-%, or at most 2.5 mole-%, on the same basis. In some embodiments, carbon dioxide may be present in the epoxidation feed gas in a concentration of from 0.10 mole-% to 10 mole-%, relative to the total epoxidation feed gas, or from 0.15 mole-% to 5 mole-%, or from 0.20 mole-% to 3 mole-%, or from 0.25 mole-% to 2.5 mole-%, on the same basis. Carbon dioxide is produced as a reaction by-product and is typically introduced into the epoxidation feed gas as an impurity (e.g., due to the use of a recycle gas stream in the epoxidation process). Carbon dioxide generally has an adverse effect on catalyst performance, with the temperature increasing as the concentration of carbon dioxide present in the epoxidation feed gas increases. Accordingly, in the commercial production of ethylene oxide, it is common for at least a portion of the carbon dioxide to be continuously removed from the recycle gas stream (e.g., via a carbon dioxide separation system) to maintain the concentration of carbon dioxide in the epoxidation feed gas at an acceptable level.

Optionally, the epoxidation feed gas may further comprise water vapor. In general, water vapor is generated within the epoxidation reactor as a combustion by-product and is typically introduced into the epoxidation reactor as an impurity in the epoxidation feed gas, due to the use of a recycle gas stream. When present, water vapor is typically present in the epoxidation feed gas in a concentration of at most 5 mole-%, relative to the total epoxidation feed gas, or at most 3 mole-%, or at most 2 mole-%, or at most 1 mole-%, or at most 0.5 mole-%, on the same basis. Alternatively, the concentration of water vapor can be expressed in terms of the partial pressure of water vapor present in the epoxidation feed gas, which may be calculated by multiplying the volume fraction (e.g., mole fraction) of water vapor present in the epoxidation feed gas at the inlet of the reactor by the reactor inlet pressure. Therefore, when present, water vapor may be present in the inlet feed gas in a concentration such that the partial pressure of water vapor in the inlet feed gas is at most 1000 kPa, or at most 50 kPa, or at most 40 kPa, or at most 35 kPa, or at most 30 kPa, or at most 25 kPa, or at most 20 kPa, or at most 15 kPa.

The epoxidation feed gas optionally may further comprise an inert gas, such as nitrogen, methane, or a combination thereof. When used, an inert gas may be added to the epoxidation feed gas to increase the oxygen flammability concentration. If desired, an inert gas may be present in the epoxidation feed gas in a concentration of at least 5 mole-%, relative to the total epoxidation feed gas, or at least 10 mole-%, or at least 20 mole-%, or at least 25 mole-%, or at least 30 mole-%, on the same basis. Similarly, an inert gas may be present in the epoxidation feed gas in a concentration of at most 80 mole-%, relative to the total epoxidation feed gas, or at most 75 mole-%, or at most 70 mole-%, or at most 65 mole-%, on the same basis. In some embodiments, an inert gas may be present in the epoxidation feed gas in a concentration of from 20 mole-% to 80 mole-%, relative to the total epoxidation feed gas, or from 30 mole-% to 70 mole-%, on the same basis.

The ethylene epoxidation process may be carried out under a broad range of operating conditions that may vary widely between different ethylene oxide plants depending, at least in part, upon the initial plant design, subsequent expansion projects, feedstock availability, the type of epoxidation catalyst used, process economics, etc. Examples of such operating conditions include, but are not limited to, temperature, reactor inlet pressure, gas flow through the epoxidation reactor (commonly expressed as the gas hourly space velocity or "GHSV"), and the ethylene oxide production rate (commonly described in terms of work rate).

To achieve reasonable commercial ethylene oxide production rates, the ethylene epoxidation reaction is typically carried out at a temperature of 180° C. or higher, or 190° C. or higher, or 200° C. or higher, or 210° C. or higher, or 225° C. or higher. Similarly, the temperature is typically 325° C. or lower, or 310° C. or lower, or 300° C. or lower, or 280° C. or lower, or 260° C. or lower. Further, the temperature may be from 180° C. to 325° C., or from 190° C. to 300° C., or from 210° C. to 300° C.

The ethylene epoxidation processes disclosed herein are typically carried out at a reactor inlet pressure of from 500 to 4000 kPa, or from 1200 to 2500 kPa, absolute. A variety of well-known devices may be used to measure the reactor inlet pressure, for example, pressure-indicating transducers, gauges, etc., may be employed. It is within the ability of one skilled in the art to select a suitable reactor inlet pressure, taking into consideration, for example, the specific type of epoxidation reactor, desired productivity, etc.

As previously mentioned, the gas flow through the epoxidation reactor is expressed in terms of the GHSV. Generally, as GHSV increases, catalyst selectivity increases for any given work rate. However, for a fixed catalyst volume, increasing GHSV generally leads to increased energy costs; therefore, there is usually an economic trade-off between higher catalyst selectivity and increased operating costs. Typically, in a gas phase epoxidation process, the GHSV is from 1,500 to 10,000 per hour.

The production rate of ethylene oxide in an epoxidation reactor is typically described in terms of work rate, which refers to the amount of ethylene oxide produced per hour per unit volume of catalyst. As is known to those skilled in the art, work rate is a function of several different variables, including, but not limited to, temperature, reactor inlet pressure, GHSV, and the composition of the epoxidation feed gas (e.g., ethylene concentration, oxygen concentration, carbon dioxide concentration, organic chloride concentration, etc.). In general, for a given set of conditions, increasing the temperature at those conditions increases the work rate, resulting in increased ethylene oxide production. However, this increase in temperature often reduces catalyst selectivity and may accelerate the aging of the catalyst. Typically, the work rate in most plants is from 50 to 400 kg of ethylene oxide per m3 of catalyst per hour (kg/m3/h), or from 120 to 350 kg/m3/h.

One skilled in the art with the benefit of the present disclosure will be able to select appropriate operating conditions, such as temperature, reactor inlet pressure, GHSV, and work rate depending upon, for example, plant design, equipment constraints, the epoxidation feed gas composition, the age of the ethylene epoxidation catalyst, etc.

Ethylene oxide produced by the ethylene epoxidation processes disclosed herein may be recovered using methods known in the art. In some embodiments, the ethylene oxide may be further reacted with water, an alcohol, carbon dioxide or an amine according to known methods to form ethylene glycol, an ethylene glycol ether, ethylene carbonate or ethanolamine, respectively, if desired.

The conversion into 1,2-ethanediol or the 1,2-ethanediol ether may comprise, for example, reacting ethylene oxide with water, suitably using an acidic or a basic catalyst. For example, for making predominantly 1,2-ethanediol and less 1,2-ethanediol ether, the ethylene oxide may be reacted with a ten-fold molar excess of water, in a liquid phase reaction in presence of an acid catalyst, e.g. 0.5 to 1.0% w sulfuric acid, based on the total reaction mixture, at a temperature of 50° C. to 70° C. and a pressure of 1 bar absolute, or in a gas phase reaction at 130° C. to 240° C. and a pressure of 20 to 40 bar absolute, preferably in the absence of a catalyst. Generally, if the proportion of water is lowered, the proportion of 1,2-ethanediol ethers in the reaction mixture increases. The 1,2-ethanediol ethers thus produced may be a di-ether, tri-ether, tetra-ether or a subsequent ether. Alternative 1,2-ethanediol ethers may be prepared by converting the ethylene oxide with an alcohol, in particular a primary alcohol, such as methanol or ethanol, by replacing at least a portion of the water by the alcohol.

The conversion into ethanolamine may comprise, for example, reacting ethylene oxide with ammonia. Anhydrous or aqueous ammonia may be used, although anhydrous ammonia is typically used to favor the production of monoethanolamine. For methods applicable in the conversion of the ethylene oxide into ethanolamine, reference may be made to, for example, U.S. Pat. No. 4,845,296, which is incorporated herein by reference.

Ethylene glycol and ethylene glycol ether may be used in a large variety of industrial applications, for example in the fields of food, beverages, tobacco, cosmetics, thermoplastic polymers, curable resin systems, detergents, heat transfer systems, etc. Ethylene carbonate may be used as, for example, a precursor in the manufacture of ethylene glycol, or as a diluent, in particular as a solvent. Ethanolamine may be used, for example, in the treating ("sweetening") of natural gas.

Having generally described the invention, a further understanding may be obtained by reference to the following examples, which are provided for purposes of illustration only and are not intended to be limiting unless otherwise specified.

Examples 1-14

Examples 1-5 for Comparison, Examples 6-14 According to the Invention

Microreactor Catalyst Testing

An ethylene epoxidation catalyst, as described in U.S. Pat. No. 4,766,105, comprising silver and a rhenium promoter deposited on an α-alumina carrier was employed in the following examples.

4.41 gram samples of crushed catalyst (14-20 mesh) were loaded into stainless steel U-shaped microreactor tubes. The ends of each tube were connected to a gas flow system allowing the flow of gas thorough the catalyst bed in a "once-through" operation. The catalyst-containing portion of each tube was immersed in a molten metal bath (heat medium) that is used to control the temperature.

For each catalyst sample, a conditioning feed gas having a composition as indicated in Table 1 was supplied to the catalyst bed at a gas flow of 1760 GHSV for a period of time between 6 and 72 hours and at a temperature between 160° C. and 245° C., as indicated in Table 1. The inlet gas pressure was 1880 kPa absolute.

Following the period of time indicated in Table 1 (the "conditioning period"), the temperature was adjusted to 235° C. and the feed gas composition was adjusted to an epoxidation feed gas as follows:

For Comparative Examples 1 and 3, because conditioning using only nitrogen resulted in a very active catalyst, the feed gas to each catalyst bed was initially adjusted after the conditioning period to an epoxidation feed gas containing 10% volume (% v) ethylene, 7% v oxygen, 3% v carbon dioxide, 3 ppmv ethyl chloride, and nitrogen balance to prevent the catalyst from running away or from operating at very high oxygen conversions. For each catalyst bed, the reactor flow was adjusted to 3850 GHSV. After 24 hours, the epoxidation feed gas supplied to each catalyst bed was adjusted to 30% v ethylene, 8.4% v oxygen, 1.26% v carbon dioxide, 1.5 ppmv ethyl chloride, and nitrogen balance. Then the temperature was adjusted so as to achieve an ethylene oxide concentration of 3.61% v in each of the outlet gas streams, which corresponded to a work rate of 273 kg/m3/h. Further, for each catalyst bed, the ethyl chloride concentration in the epoxidation feed gas was adjusted between 1 and 5 ppmv so as to obtain a maximum selectivity at a constant ethylene oxide concentration of 3.61% v in each of the outlet gas streams.

For Comparative Examples 2, 4-5 and Examples 6-14, after the conditioning period, the feed gas to each catalyst bed was adjusted to an epoxidation feed gas containing 30% v ethylene, 8.4% v oxygen, 1.26% v carbon dioxide, 3 ppmv ethyl chloride, and nitrogen balance. For each catalyst bed, the reactor flow was adjusted to 3850 GHSV and the temperature was held constant for about 24 hours to allow for catalyst equilibration, after which the temperature was adjusted so as to achieve an ethylene oxide concentration of 3.61% v in each of the outlet gas streams, which corresponded to a work rate of 273 kg/m3/h. Further, for each catalyst bed, the ethyl chloride concentration in the epoxidation feed gas was adjusted between 1 and 5 ppmv so as to obtain a maximum selectivity at a constant ethylene oxide concentration of 3.61% v in each of the outlet gas streams.

All examples were run out to 0.15 kT/m3 cumulative ethylene oxide production ("kT/m3 CumEO") while maintaining a constant ethylene oxide concentration of 3.61% V in the outlet gas stream and adjusting ethyl chloride concentration to achieve maximum selectivity.

For purposes of catalyst testing and comparison, catalyst age may be conveniently expressed in terms of the total cumulative production of ethylene oxide on a mass basis (e.g., using metric kilotons "kT") divided by the catalyst-packed reactor volume (e.g., in cubic meters "m3"). Accordingly, Table 1 provides the performance for each of Comparative Examples 1-5 and Examples 6-14 in terms of the maximum selectivity that was achieved between 0.07-0.15 kT/m3 CumEO, which corresponded to approximately 11-22 days on stream. In addition, FIG. 1A is a bar chart of Experiments 1-14, which shows an average selectivity of 85.7% for Comparative Examples 1-5, an average selectivity of 86.9% for the Examples 6 and 7 (at low temperature), and an average selectivity of 88.4% for Examples 8-14.

As will be appreciated by one of skill in the art, the "activity" of an ethylene epoxidation catalyst generally refers to the reaction rate of ethylene towards ethylene oxide per unit of ethylene epoxidation catalyst volume in the epoxidation reactor and is typically expressed as the temperature required to maintain a given ethylene oxide production rate. Therefore, with respect to Table 1 below, the activity is expressed as the temperature that was required to maintain a constant ethylene oxide concentration of 3.61% v in the outlet gas stream, which corresponded to a work rate of 273 kg/m3/h.

selectivity than the same ethylene epoxidation catalyst would otherwise achieve using a conventional catalyst conditioning method.

Comparative Examples 1-4 demonstrate conditioning without oxygen, using inert gases (e.g. nitrogen, ethylene) at a temperature between 160° C. and 245° C. As can be seen in Table 1, these Comparative Examples resulted in similar selectivities (86.0, 85.7, 85.7 and 85.5%). Comparative Example 5 utilized oxygen in the conditioning feed gas at a temperature of 160° C. As can be seen in Table 1, this resulted in a selectivity similar to all other Comparative Examples including Comparative Example 4, which was also conducted at 160° C. but with a conditioning gas comprising ethylene.

Examples 6 and 7 demonstrate a selectivity improvement as a result of conditioning using a conditioning feed gas comprising 0.5 and 5% oxygen, respectively, at 185° C. As can be seen from Table 1, selectivity improved to 86.8-86.9 as compared to all of the Comparative Examples, and in particular as compared to Comparative Example 1, which was conducted at the same temperature and time period in the absence of oxygen and achieved only 86% selectivity.

Figure 1B:
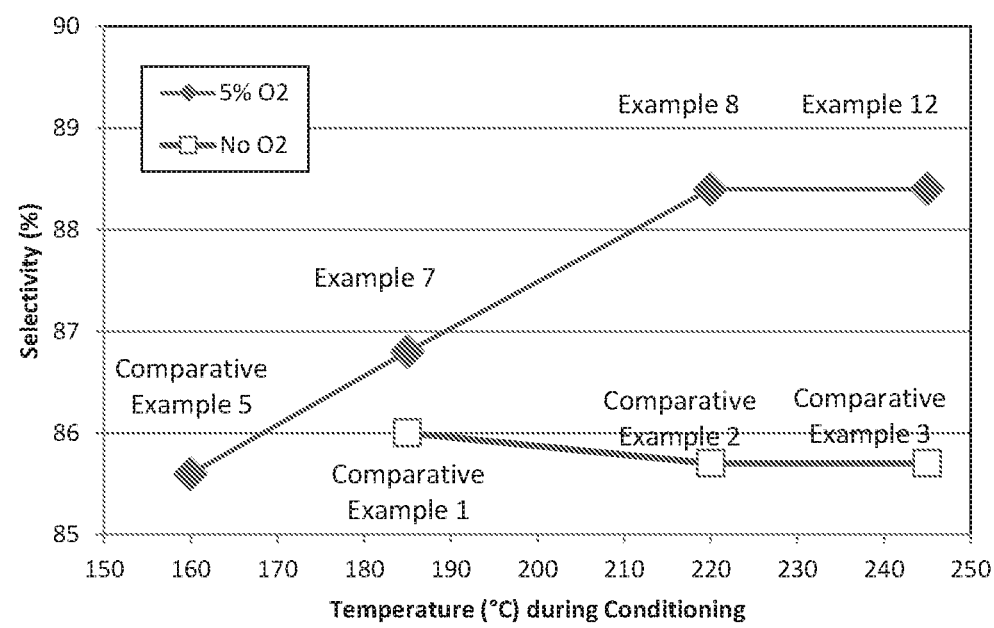
FIG. 1B shows the effect of the temperature during conditioning for an oxygen concentration of 5% for a period of 24 hours.

Examples 7, 8 and 12 and Comparative Example 5 demonstrate the effect of temperature on selectivity using a conditioning feed gas comprising oxygen. Comparative Example 5 utilized oxygen in the conditioning feed gas at a temperature of 160° C. As shown in Table 1 and FIG. 1B, the selectivity for Comparative Example 5 was not improved, but instead was similar to Comparative Examples 1-4. Example 7 demonstrates that conditioning using a conditioning feed gas comprising oxygen at the temperature of 185° C. is effective in improving catalyst selectivity as compared to Comparative Examples 1-5 and in particular as compared to Comparative Example 5, which was conducted at the same oxygen concentration for the same amount of time at 160° C. Selectivity in Example 7 was 86.8% versus Comparative Example 5, which gave a selectivity of only 85.6%. Furthermore, increasing the temperature to 220° C. as in Example 8 resulted in a further increase in selectivity

TABLE 1

| Ex. No. | Conditioning Feed Gas Composition | | | | | At 0.07-0.15 kT/m³ CumEO | |
|---|---|---|---|---|---|---|---|
| | $O_2$ Conc. (mole-%) | $C_2H_4$ Conc. (mole-%) | $N_2$ Conc. (mole-%) | Temp. (° C.) during Conditioning | Time (h) of Conditioning | Max Selectivity (mole-%) | Activity (° C.) |
| 1 Comp | — | — | 100 | 185 | 24 | 86.0 | 249 |
| 2 Comp | — | — | 100 | 220 | 24 | 85.7 | 251 |
| 3 Comp | — | — | 100 | 245 | 24 | 85.7 | 249 |
| 4 Comp | — | 30 | Balance | 160 | 24 | 85.5 | 248 |
| 5 Comp | 5 | — | Balance | 160 | 24 | 85.6 | 248 |
| 6 | 0.5 | — | Balance | 185 | 24 | 86.9 | 250 |
| 7 | 5 | — | Balance | 185 | 24 | 86.8 | 250 |
| 8 | 5 | — | Balance | 220 | 24 | 88.4 | 248 |
| 9 | 0.5 | — | Balance | 245 | 6 | 88.5 | 249 |
| 10 | 0.5 | — | Balance | 245 | 24 | 88.4 | 250 |
| 11 | 5 | — | Balance | 245 | 6 | 88.4 | 253 |
| 12 | 5 | — | Balance | 245 | 24 | 88.4 | 252 |
| 13 | 5 | — | Balance | 245 | 72 | 88.6 | 253 |
| 14 | 21 | — | Balance | 245 | 24 | 88.2 | 249 |

Examples 6-14 (according to the invention), compared with Examples 1-5 (comparative), demonstrate that after contacting the ethylene epoxidation catalyst with a conditioning feed gas comprising oxygen at a temperature that is above 180° C., in the absence of ethylene, the ethylene epoxidation catalyst achieves a higher maximum catalyst to 88.4%. Further increasing the temperature to 245° C. as in Example 12 also resulted in selectivity of 88.4%.

Figure 1C:
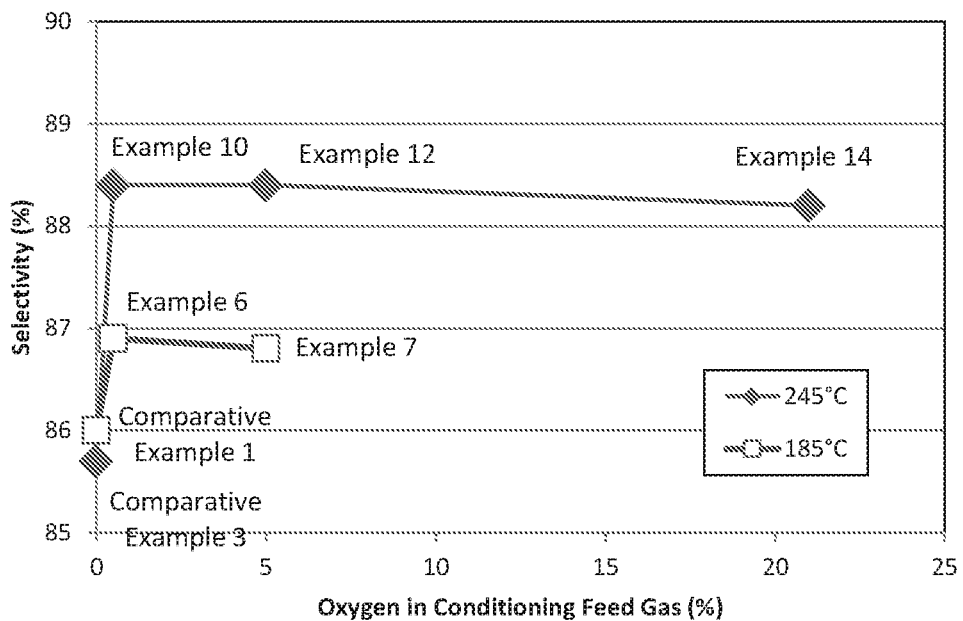
FIG. 1C shows the effect of oxygen concentration for two temperatures, 185° C. and 245° C., for a period of 24 hours.

Examples 6, 7, 10, 12 and 14, which were all conducted for 24 hours, demonstrate a selectivity improvement across a range of oxygen concentrations (0.5%, 5% and 21%) at multiple temperatures (185° C. and 245° C.), as shown in FIG. 1C. All of these examples demonstrated an improvement in selectivity as compared to Comparative Examples 1-5, and in particular as compared to Comparative Examples 1 and 3, which were conditioned with an inert gas at 185° C. and 245° C., respectively.

Figure 1D:
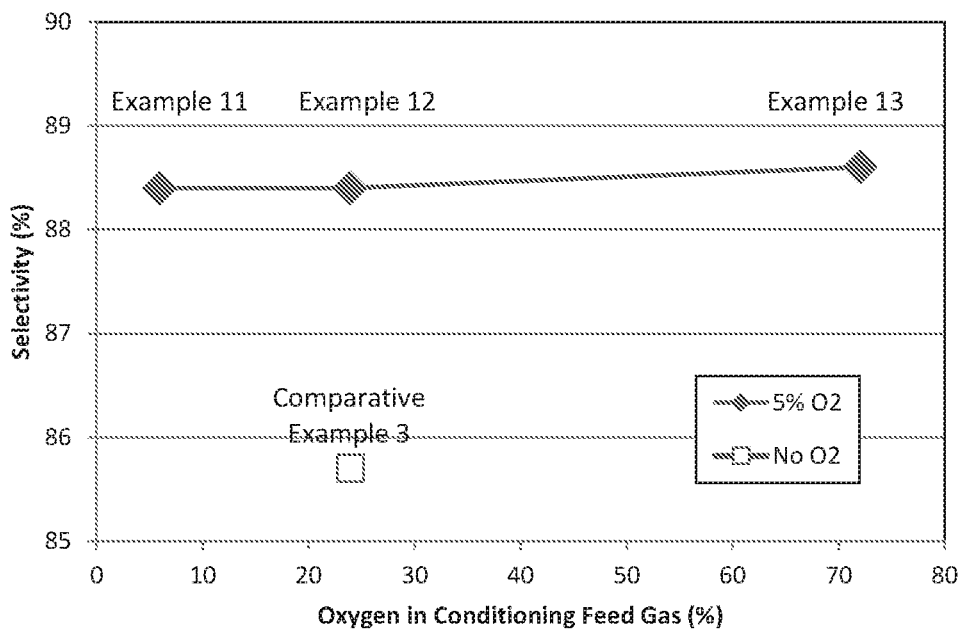
FIG. 1D shows the effect of conditioning time at a temperature of 245° C.

Furthermore, Examples 11, 12 and 13, which were all conducted at a temperature of 245° C. and at an oxygen concentration of 5%, demonstrate a selectivity improvement across a range of times (6, 24 and 72 hours). All of these examples demonstrated an improvement in selectivity as compared to Comparative Example 3, as shown in FIG. 1D. It is expected that very long conditioning times of for example 100 and 200 or more hours would also be effective, but perhaps not practical when balanced against with the economic impact of not having any ethylene oxide produced during an oxygen conditioning period.

Examples 15-17

Additional Microreactor Catalyst Testing

An ethylene epoxidation catalyst, as described in U.S. Pat. No. 4,766,105, comprising silver and a rhenium promoter deposited on an α-alumina carrier was employed in the following examples.

4.41 gram samples of crushed catalyst (14-20 mesh) were loaded into stainless steel U-shaped microreactor tubes. The ends of each tube were connected to a gas flow system allowing the flow of gas thorough the catalyst bed in a "once-through" operation. The catalyst-containing portion of each tube was immersed in a molten metal bath (heat medium) at 245° C.

For Example 15, a conditioning feed gas comprising 5% v oxygen, 2 ppmv ethyl chloride and nitrogen balance was supplied to the catalyst bed at a gas flow of 1760 GHSV for a period of 24 hours at 245° C. The inlet gas pressure was 1880 kPa absolute.

After supplying the conditioning feed gas for a period of 24 hours, the temperature was adjusted to 235° C. and the feed gas composition was adjusted to an epoxidation feed gas containing 30% v ethylene, 8.4% v oxygen, 1.26% v carbon dioxide, 3.0 ppmv ethyl chloride and nitrogen balance. The reactor flow was adjusted to 3850 GHSV and the temperature was held constant for about 24 hours to allow for catalyst equilibration, after which the temperature was adjusted so as to achieve an ethylene oxide concentration of 3.61% v in the outlet gas stream, which corresponded to a work rate of 273 kg/m3/h. Further, the ethyl chloride concentration in the feed gas was adjusted between 1 and 5 ppmv so as to obtain a maximum selectivity at a constant ethylene oxide concentration of 3.61% v in the outlet gas stream.

For Example 16, prior to the introduction of a conditioning feed gas, a sweeping gas comprising 100 mole-% nitrogen was supplied to the catalyst bed at a gas flow of 1760 GHSV for a period of 24 hours. The inlet gas pressure was 1880 kPa absolute. After supplying the sweeping gas for a period of 24 hours, the temperature was adjusted to 245° C. and a conditioning feed gas comprising 5% v oxygen and nitrogen balance was supplied to the catalyst bed at a gas flow of 1760 GHSV for a period of 24 hours at 245° C. The inlet gas pressure was 1880 kPa absolute.

After supplying the conditioning feed gas for a period of 24 hours, the temperature was adjusted to 235° C. and the feed gas composition was adjusted to an epoxidation feed gas containing 30% v ethylene, 8.4% v oxygen, 1.26% v carbon dioxide, and nitrogen balance. The reactor flow was adjusted to 3850 GHSV and the temperature was held constant for about 24 hours to allow for catalyst equilibration, after which the temperature was adjusted so as to achieve an ethylene oxide concentration of 3.61% v in the outlet gas stream, which corresponded to a work rate of 273 kg/m3/h. Further, the ethyl chloride concentration in the epoxidation feed gas was adjusted between 1 and 5 ppmv so as to obtain a maximum selectivity at a constant ethylene oxide concentration of 3.61% v in the outlet gas stream.

For Example 17, a conditioning feed gas comprising 5% v oxygen and nitrogen balance was supplied to the catalyst bed at a gas flow of 1760 GHSV for a period of 24 hours at 245° C. The inlet gas pressure was 1880 kPa absolute. After supplying the conditioning feed gas for a period of 24 hours, the temperature was adjusted to 235° C. and the feed gas composition was adjusted to an epoxidation feed gas containing 10% v ethylene, 7% v oxygen, 3% v carbon dioxide, 3.0 ppmv ethyl chloride, and nitrogen balance. The reactor flow was adjusted to 3850 GHSV and the temperature was held constant for about 12 hours to allow for catalyst equilibration, after which the temperature was ramped to 260° C. over a period of 11 hours and then held constant at 260° C. for the following 48 hours to accomplish a heat treatment.

At the end of the 48 hour period, the temperature was adjusted to 250° C. and the epoxidation feed gas was adjusted to 35% v ethylene, 8.4% v oxygen, 1.26% v carbon dioxide, 3.0 ppmv ethyl chloride, and nitrogen balance. The reactor flow was adjusted to 3850 GHSV and the temperature was adjusted so as to achieve an ethylene oxide concentration of 3.61% v in the outlet gas stream, which corresponded to a work rate of 273 kg/m3/h. Further, the ethyl chloride concentration in the feed gas was adjusted between 1 and 5 ppmv so as to obtain a maximum selectivity at a constant ethylene oxide concentration of 3.61% v in the outlet gas streams.

Examples 15-17 were run out to 0.15 kT/m3 CumEO while maintaining a constant ethylene oxide concentration of 3.61% V in the outlet gas stream and adjusting ethyl chloride concentration to achieve maximum selectivity. Table 2 provides the performance for Examples 15-17 in terms of the maximum selectivity that was achieved between 0.07-0.15 kT/m3 cumulative ethylene oxide production, which corresponded to approximately 11-22 days on stream.

TABLE 2

| | Conditioning Feed Gas Composition | | | Temp. | | | | At 0.07-0.15 kT/m$^3$ CumEO | |
| --- | --- | --- | --- | --- | --- | --- | --- | --- | --- |
| Ex. No. | $O_2$ Conc. (mole-%) | $N_2$ Conc. (mole-%) | Ethyl Chloride (ppmv) | (° C.) during Conditioning | Time (h) of Conditioning | Use of Sweeping Gas? | Heat Treatment Performed? | Max Selectivity (mole-%) | Activity (° C.) |
| 15 | 5 | Balance | 2 | 245 | 24 | No | No | 88.0 | 247 |
| 16 | 5 | Balance | — | 245 | 24 | Yes | No | 88.2 | 247 |
| 17 | 5 | Balance | — | 245 | 24 | No | Yes | 88.5 | 247 |

Example 15 demonstrates that a conditioning method of the present disclosure, which utilizes a conditioning feed gas comprising oxygen and an organic chloride, provides an ethylene epoxidation catalyst that achieves a higher maximum catalyst selectivity (88.0%) than the same ethylene epoxidation catalyst would otherwise achieve using a conventional catalyst conditioning method, such as that of Comparative Example 3 (85.7%).

Example 16 demonstrates that a conditioning method of the present disclosure, wherein an ethylene epoxidation catalyst is contacted with an optional nitrogen sweeping gas prior to conditioning, provides an ethylene epoxidation catalyst that achieves a higher maximum catalyst selectivity (88.2%) than the same ethylene epoxidation catalyst would otherwise achieve using a conventional catalyst conditioning method, such as that of Comparative Example 3 (85.7%).

Example 17 demonstrates that a conditioning method of the present disclosure, wherein an ethylene epoxidation catalyst is subjected to an optional heat treatment after conditioning, provides an ethylene epoxidation catalyst that achieves a higher maximum catalyst selectivity (88.5%) than the same ethylene epoxidation catalyst would otherwise achieve using a conventional catalyst conditioning method, such as that of Comparative Example 3 (85.7%).

Examples 18-19

Example 18 for Comparison, Example 19 According to the Invention

Microreactor Catalyst Testing

An ethylene epoxidation catalyst, as described in U.S. Pat. No. 4,766,105, comprising silver and a rhenium promoter deposited on an α-alumina carrier was employed in the following examples.

4.41 gram samples of crushed catalyst (14-20 mesh) were loaded into stainless steel U-shaped microreactor tubes. The ends of each tube were connected to a gas flow system allowing the flow of gas thorough the catalyst bed in a "once-through" operation. The catalyst-containing portion of each tube was immersed in a molten metal bath (heat medium) at 245° C.

For Comparative Example 18, a conditioning feed gas comprising 100 mole-% nitrogen was supplied to the catalyst bed at a gas flow of 1760 GHSV for a period of 24 hours at 245° C. The inlet gas pressure was 1880 kPa absolute.

For Example 19, a conditioning feed gas comprising 5% v oxygen and nitrogen balance was supplied to the catalyst bed at a gas flow of 1760 GHSV for a period of 24 hours at 245° C. The inlet gas pressure was 1880 kPa absolute.

For both catalyst beds, after supplying the conditioning feed gas for a period of 24 hours, the temperature was adjusted to 235° C. and the feed gas composition was adjusted to an epoxidation feed gas containing 30% v ethylene, 8.4% v oxygen, 1.26% v carbon dioxide, 3.0 ppmv ethyl chloride and nitrogen balance. For both catalyst beds, the reactor flow was adjusted to 3850 GHSV and the temperature was held at 235° C. Oxygen conversion and selectivity were then monitored for the next 12 hours.

Figure 2A:
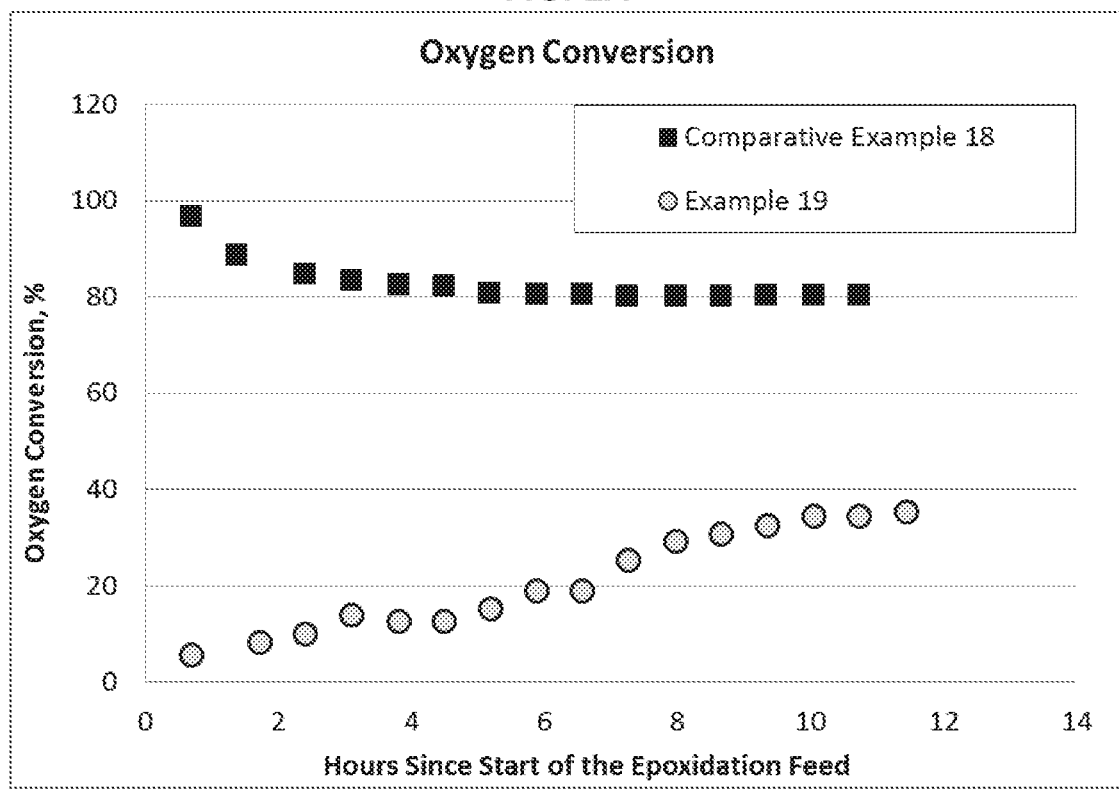
FIG. 2A is a graph depicting oxygen conversion (%) in the first 12 hours after the introduction of an epoxidation feed gas, as observed in Comparative Example 18 and Example 19, hereinafter.
Figure 2B:
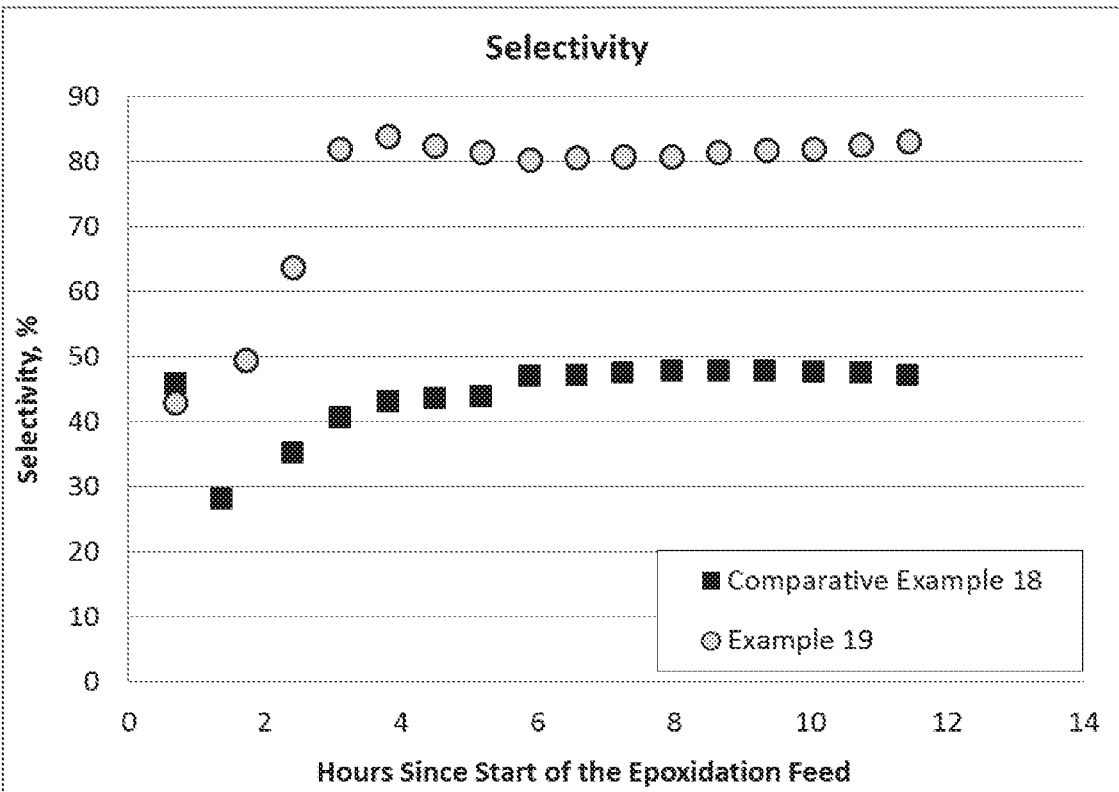
FIG. 2B is a graph depicting selectivity (%) in the first 12 hours after the introduction of an epoxidation feed gas, as observed in Comparative Example 18 and Example 19, hereinafter.

Reference is made to FIGS. 2A and 2B, which depict oxygen conversion and selectivity of Comparative Example 18 and Example 19 in the first 12 hours after the introduction of an epoxidation feed gas. As can be seen from FIG. 2A in Example 19, contacting the catalyst bed with a conditioning feed gas comprising 5% oxygen at a temperature of 245° C. oxygen for a period of 24 hours resulted in a very low oxygen conversion starting with an initial oxygen conversion of about 8% and gradually rising to about 35% in the course of the first 12 hours of the epoxidation reaction. This is in contrast to Comparative Example 18, which was not contacted with a conditioning feed gas comprising oxygen, resulting in a very high initial oxygen conversion of about 97% and gradually decreasing to 80%. As will be appreciated by one of skill in the art, a high oxygen conversion is undesirable as it can result in a reactor runaway, a hot spot in the catalyst bed, decompositions and other effects that could compromise safety and the ability of the plant operator to control the epoxidation process. High oxygen conversion can also result in the irreversible damage to the catalyst. A plant operator would usually have to take steps to avoid high oxygen conversion scenarios by limiting oxygen and/or ethylene feed rates and concentrations or take additional time to deactivate catalysts. This would lead to a much longer start-up time before full production rate and final ethylene and/or oxygen concentrations, which are the same or substantially the same as those in the epoxidation feed gas utilized during normal ethylene oxide production, are achieved.

In addition, as can be seen from FIG. 2B, Example 19 achieved a high selectivity of approximately 82% in the 2 hours after introduction of an epoxidation feed gas, as compared to Comparative Example 18, which only achieved approximately 40% selectivity in 2 hours which gradually improved to only about 48% in the next 10 hours. Increased selectivity is obviously an important economic benefit of the present disclosure.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. While compositions and methods/processes are described in terms of "comprising," "containing," or "including" various components or steps, the compositions and methods/processes can also "consist essentially of" or "consist of" the various components and steps. All numbers and ranges disclosed above may vary by some amount. Whenever a numerical range with a lower limit and an upper limit is disclosed, any number and any included range falling within the range are specifically disclosed. In particular, every range of values (of the form, "from a to b," or, equivalently, "from a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

That which is claimed is:

1. A method for the conditioning of an ethylene epoxidation catalyst comprising:
    contacting an ethylene epoxidation catalyst comprising a carrier, having silver and a rhenium promoter deposited thereon, with a conditioning feed gas consisting essentially of oxygen, an inert gas and, optionally, an organic chloride, for a period of time of from 6 to 72 hours at a temperature that is, from at least 185° C. and at most 220° C., wherein the contacting of the ethylene epoxidation catalyst with the conditioning feed gas occurs in a catalyst bed within an epoxidation reactor and in the absence of ethylene, and wherein the catalyst bed comprises the ethylene epoxidation catalyst.

2. The method of claim 1 wherein the conditioning feed gas comprises oxygen in a concentration of from 0.5 to 21 mole %, relative to the total conditioning feed gas.

3. The method of claim 1 wherein the period of time is from 12 to 72 hours.

4. The method of claim 1 wherein the period of time is from 24 hours to 72 hours.

5. The method of claim 1 further comprising contacting the ethylene epoxidation catalyst with a sweeping gas.

6. The method of claim 1, wherein the inert gas is selected from nitrogen, methane, argon, helium, and a combination thereof.

* * * * *